United States Patent
Oshima et al.

(10) Patent No.: US 6,239,150 B1
(45) Date of Patent: *May 29, 2001

(54) PENICILLAMINAMIDE DERIVATIVES

(75) Inventors: Masahiro Oshima; Norimichi Iwase; Naoto Inakoshi; Koichi Sugawara; Misao Okitsu, all of Kanagawa (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/983,321

(22) PCT Filed: Jul. 19, 1996

(86) PCT No.: PCT/JP96/02027

§ 371 Date: Mar. 12, 1998

§ 102(e) Date: Mar. 12, 1998

(87) PCT Pub. No.: WO97/05108

PCT Pub. Date: Feb. 13, 1997

(30) Foreign Application Priority Data

Jul. 26, 1995 (JP) .................................................. 7-190651

(51) Int. Cl.[7] ...................... C07D 207/16; C07D 211/60; A61K 31/40; A61K 31/445
(52) U.S. Cl. .......................... 514/330; 514/423; 546/226; 548/537
(58) Field of Search ...................................... 514/330, 423; 546/226; 548/537

(56) References Cited

U.S. PATENT DOCUMENTS

| | | | |
|---|---|---|---|
| 5,510,369 | 4/1996 | Lumma et al. | 514/422 |
| 5,602,253 | 2/1997 | Antonsson et al. | 544/330 |
| 5,672,582 | 9/1997 | Veber et al. | 514/19 |
| 5,723,444 | 3/1998 | Antonsson et al. | 514/19 |
| 5,744,487 | 4/1998 | Ohshima et al. | 514/326 |

FOREIGN PATENT DOCUMENTS

| | | |
|---|---|---|
| 2140598 | 10/1995 | (CA) . |
| 0669317 | 8/1995 | (EP) . |
| 211978 | 6/1995 | (HU) . |
| 4-89498 | 3/1992 | (JP) . |
| 4330094 | 11/1992 | (JP) . |
| 6-25195 | 2/1994 | (JP) . |
| 6298795 | 10/1994 | (JP) . |
| 7252217 | 10/1995 | (JP) . |
| 9315756 | 8/1993 | (WO) . |
| 9408941 | 4/1994 | (WO) . |
| 9425049 | 11/1994 | (WO) . |
| 9425051 | 11/1994 | (WO) . |
| 94/29336 | 12/1994 | (WO) . |
| 96/03374 | 2/1996 | (WO) . |

OTHER PUBLICATIONS

Bagdy et al., *Folia Haematol.* vol. 109,22 (1982).
Markwardt et al., *Thromb. Res.*, vol. 17, 425 (1980).
Bajusz et al., *Journal of Med Chem.*, vol. 33, 1729 (1990).
Kettner et al., *J. Biol. Chem.*, vol. 265, 18289 (1990).
"Jikken Kagaku Koza", 4th ed. vol. 22, *Organic Synthesis IV*, p. 259–271(1992).
Nubuo, I., et al., "Fundamentals and Experiments of Peptide Synthesis", Maruzen, pp. 142–171 (1985).
Abstract of South African Patent No. 92/2022, published Sep. 28, 1992.

*Primary Examiner*—Richard L. Raymond
*Assistant Examiner*—Deepak Rao
(74) *Attorney, Agent, or Firm*—Greenblum & Bernstein, P.L.C.

(57) ABSTRACT

Compounds represented by the general formula (I) wherein n represents 1 or 2; $R^1$ represents, for example, a $C_1$–$C_{10}$ alkyl group which may be substituted with a $C_3$–$C_{10}$ cycloalkyl group or carboxyl group; $R^2$ represents hydrogen atom, a $C_1$–$C_{10}$ alkyl group or other; and $R^3$ represents amino group or amidino group, whose example include trans-4-amino-[(S)-N-[(S)-2-propoxycarbonylamino-3-isopropylthio-3-methyl-butanoyl]prolyl]aminomethylcyclohexane. The compounds have potent inhibitory activity against thrombin, and are useful as anticoagulants.

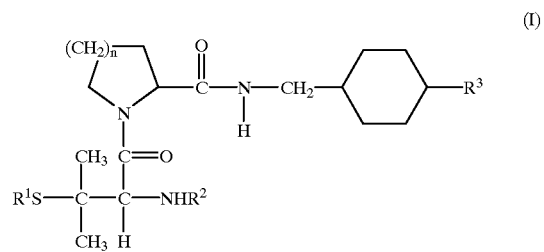

(I)

12 Claims, No Drawings

PENICILLAMINAMIDE DERIVATIVES

This application is a 371 of PCT/JP96/02027 filed Jul. 19, 1996.

TECHNICAL FIELD

The present invention relates to novel penicillaminamide derivatives. More specifically, the present invention relates to penicillaminamide derivatives and salts thereof which have inhibitory activity against proteases, in particular, antithrombotic activity. The present invention also relates to protease inhibitors comprising said substances as active ingredients.

BACKGROUND ART

It is well known that various kinds of proteases exist in living bodies. For example, the existence of a class of serine proteases such as thrombin, factor Xa, factor IXa, factor VIIa, trypsin, plasmin, tissue plasminogen activator, kallikrein, C1 enzyme in complement, C3/C5 convertase, and tryptase are known. It is also known that various kinds of diseases are caused when these proteases are abnormally activated by. Accordingly, substances having inhibitory activity against these proteases are expected to be useful as medicaments.

For example, it is known that antithrombotic agents are effective as therapeutic medicaments for thrombosis, and for this reason, developments of protease inhibitors having antithrombotic activity have been progressing. However, these inhibitors have several problems of, for example, insufficient stability in vivo or non-selectivity to serine proteases other than thrombin, or decrease of antithrombotic activity when administered orally. Therefore, the inhibitors are not satisfactory for practical applications.

Some tripeptide derivatives containing a moiety of arginine derivative are also known as protease inhibitors. For example, D-phenylalanyl-L-prolyl-L-arginal is known as a thrombin inhibitor (for example, Folia Haematol. 109, 22 (1982)). However, this compound is relatively unstable in a living body (J. Med. Chem., 33, 1729 (1990)). There are also several reports about arginal derivatives (Japanese Patent Unexamined Publication No. (Hei)4-89498/1992; and WO 9315756), amidinophenyl-alanine derivatives (Thromb. Res., 17, 425 (1980)), arginine ketoamide derivatives (WO 9408941), boron compound derivatives (For example, J. Biol. Chem., 265, 18289 (1990), Japanese Patent Unexamined Publication Nos. Hei 4-330094/1992 and (Hei)6-298795/1994, and WO 9425049). However, the derivatives have a problem in that they have low enzymatic selectivity among serine proteases belonging to thrombin homologue, in particular, trypsin. Guanidine derivatives (Japanese Patent Unexamined Publication No. (Hei)6-25195/1994) and tetrasubstituted cyclohexylamine derivatives (WO 9425051) were reported as thrombin-specific inhibitors, however, their efficacy cannot be expected by oral administration.

Under the above-described circumstances, the inventor of the present invention conducted various research to find substances which have practically satisfactory enzyme selectivity, oral availability, and stability in vivo, and are structurally novel. As a result, they found that the penicillaminamide derivatives set forth below have desired properties, and thus achieved the present invention.

The present invention provides penicillaminamide derivatives represented by the following general formula (I) and salts thereof, and hydrates thereof and solvates thereof:

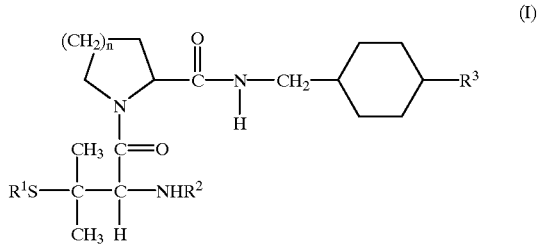

wherein:
n represents 1 or 2;
$R^1$ represents a $C_1$–$C_{10}$ alkyl group which may be substituted with a $C_3$–$C_{10}$ cycloalkyl group or carboxyl group, a $C_6$–$C_{10}$ aryl group which may be substituted, a $C_3$–$C_{10}$ cycloalkyl group which may be substituted, or a $C_7$–$C_{12}$ aralkyl group which may be substituted;
$R^2$ represents hydrogen atom, a $C_1C_{10}$ alkyl group, a $C_7$–$C_{12}$ aralkyl group which may be substituted, —$COR^4$ (wherein $R^4$ represents hydrogen atom, a $C_1$–$C_{10}$ alkyl group, a $C_1$–$C_{10}$ alkoxy group, a $C_6$–$C_{10}$ aryl group which may be substituted, a $C_6$–$C_{10}$ aryloxy group which may be substituted, a $C_3$–$C_{10}$ cycloalkyl group which may be substituted, a $C_3$–$C_{10}$ cycloalkyloxy group which may be substituted, a $C_7$–$C_{12}$ aralkyl group which may be substituted, or a $C_7$–$C_{12}$ aralkyloxy group), or —$SO_2R^5$ (wherein $R^5$ represents a $C_1$–$C_1$ alkyl group, a $C_6$–$C_{10}$ aryl group which may be substituted, a $C_3$–$C_{10}$ cycloalkyl group which may be substituted, or a $C_7$–$C_{12}$ aralkyl group which may be substituted), and
$R^3$ represents amino group or amidino group, provided that the compounds wherein:
$R^1$ represents methyl group, $R^2$ represents ethoxycarbonyl group, $R^3$ represents amino group, and n represents 1;
$R^1$ represents methyl group, $R^2$ represents methylsulfonyl group, $R^3$ represents amino group, and n represents 1;
$R^1$ represents ethyl group, $R^2$ represents methylsulfonyl group, $R^3$ represents amino group, and n represents 1; and
$R^1$ represents isopropyl group, $R^2$ represents ethoxycarbonyl group, $R^3$ represents amidino group, and n represents 1 are excluded.

According to other aspects of the present invention, there are provided medicament comprising a substance selected from the group consisting of the aforementioned penicillaminamide derivatives and salts thereof, and hydrates thereof and solvates thereof; and pharmaceutical compositions comprising a substance selected from the group consisting of the aforementioned penicillaminamide derivatives and salts thereof, and hydrates thereof and solvates thereof as an active ingredient, together with a pharmaceutically acceptable carrier. The aforementioned medicaments and pharmaceutical compositions are useful for preventive and/or therapeutic treatment of diseases caused by hyperfunction of protease activity, for example, they are useful as antithrombotic agents, i.e., orally available anticoagulant agents. Protease inhibitors comprising a substance selected from the group consisting of the aforementioned penicillaminamide derivatives and salts thereof, and hydrates thereof and solvates thereof are also provided according to further aspect of the present invention.

According to still further aspects of the present invention, there are provided a use of a substance selected from the group consisting of the aforementioned penicillaminamide derivatives and salts thereof, and hydrates thereof and solvates thereof for the manufacture of the above-described pharmaceutical compositions; and a method for therapeutic treatment of a disease caused by hyperfunction of protease activity, which comprises administering to a patient a therapeutically and/or preventively effective amount of a substance selected from the group consisting of the aforementioned penicillaminamide derivatives and salts thereof, and hydrates thereof and solvates thereof.

DETAILED DESCRIPTION

The penicillaminamide derivatives of the present invention are represented by the formula (I) mentioned above.

Examples of the $C_1$–$C_{10}$ alkyl group in the above definition include, for example, methyl group, ethyl group, n-propyl group, i-propyl group, n-butyl group, s-butyl group, i-butyl group, t-butyl group, n-pentyl group, 1,1-dimethylpropyl group, neopentyl group, n-hexyl group, 1-methyl-1-ethylpropyl group, n-heptyl group, 1,1-diethylpropyl group, n-octyl group, n-nonyl group, and n-decyl group.

Examples of the $C_6$–$C_{10}$ aryl group include, for example, phenyl group, tolyl group, and naphthyl group.

Examples of the $C_3$–$C_{10}$ cycloalkyl group include, for example, cyclopropyl group, cyclobutyl group, cyclopentyl group, cyclohexyl group, cycloheptyl group, cyclooctyl group, cyclononyl group, and cyclodecyl group. Examples of the $C_1$–$C_{10}$ alkoxy group include, for example, methoxy group, ethoxy group, n-propoxy group, i-propoxy group, n-butoxy group, s-butoxy group, i-butoxy group, t-butoxy group, n-pentyloxy group, neopentyloxy group, n-hexyloxy group, n-heptyloxy group, n-octyloxy group, n-nonyloxy group, and n-decyloxy group. Examples of the $C_3$–$C_{10}$ cycloalkyloxy group include, for example, cyclopropyloxy group, cyclobutyloxy group, cyclopentyloxy group, cyclohexyloxy group, and cycloheptyloxy group. Examples of the $C_7$–$C_{12}$ aralkyloxy group include, for example, benzyloxy group, phenylethyloxy group, phenylpropyloxy group, and naphthylmethyloxy group, and examples of the $C_6$–$C_{10}$ aryloxy group include, for example, phenyloxy group, tolyloxy group, and naphthyloxy group.

Examples of the $C_7$–$C_{12}$ aralkyl group include, for example, benzyl group, phenylethyl group, phenylpropyl group, and naphthylmethyl group.

When the definitions of the functional groups of the aforementioned general formula refer to "which may be substituted," examples of the substituents include, for example, a $C_1$–$C_6$ alkyl group such as methyl group, ethyl group, n-propyl group, isopropyl group, n-butyl group, s-butyl group, isobutyl group, t-butyl group, n-pentyl group, and n-hexyl group; a $C_1$–$C_6$ haloalkyl group such as chloromethyl group, bromomethyl group, dichloromethyl group, 1-chloroethyl group, 2-chloroethyl group, 3-chloropropyl group, 4-chlorobutyl group, 5-chloropentyl group, 6-chlorohexyl group, difluoromethyl group, and trifluoromethyl group; a $C_1$–$C_6$ alkoxy group such as methoxy group, ethoxy group, n-propoxy group, isopropoxy group, n-butoxy group, s-butoxy group, isobutyloxy group, t-butyloxy group, n-pentyloxy group, and n-hexyloxy group; hydroxyl group; carboxyl group; a $C_2$–$C_7$ carboxyalkyl group such as carboxymethyl group, 2-carboxyethyl group, 3-carboxypropyl group, 4-carboxybutyl group, 5-carboxypentyl group, and 6-carboxyhexyl group; a $C_2$–$C_7$ carboxyalkyloxy group such as carboxymethoxy group, 2-carboxyethoxy group, 3-carboxypropoxy group, 4-carboxybutyloxy group, 5-carboxypentyloxy group, and 6-carboxyhexyloxy group; a $C_2$–$C_7$ acyl group such as acetyl group, propionyl group, butyryl group, isobutyryl group, valeryl group, isovaleryl group, pivaloyl group, hexanoyl group, and heptanoyl group; a $C_2$–$C_7$ acyloxy group such as acetyloxy group, propionyloxy group, butyryloxy group, isobutyryloxy group, valeryloxy group, isovaleryloxy group, pivaloyloxy group, hexanoyloxy group, and heptanoyloxy group; a $C_2$–$C_7$ alkoxycarbonyl group such as methoxycarbonyl group, ethoxycarbonyl group, n-propoxycarbonyl group, isopropoxycarbonyl group, n-butyloxycarbonyl group, s-butyloxycarbonyl group, isobutyloxycarbonyl group, t-butyloxycarbonyl group, n-pentyloxycarbonyl group, and n-hexyloxycarbonyl group; a $C_2$–$C_7$ alkoxycarbonyloxy group such as methoxycarbonyloxy group, ethoxycarbonyloxy group, n-propoxycarbonyloxy group, isopropoxycarbonyloxy group, n-butyloxycarbonyloxy group, s-butyloxycarbonyloxy group, isobutyloxycarbonyloxy group, t-butyloxycarbonyloxy group, n-pentyloxycarbonyloxy group, and n-hexyloxycarbonyloxy group; a $C_8$–$C_{10}$ aralkyloxycarbonyl group such as benzyloxycarbonyl group, phenylethyloxycarbonyl group, and phenylpropyloxycarbonyl group; a $C_3$–$C_9$ alkoxycarbonylalkoxy group such as methoxycarbonylmethoxy group, ethoxycarbonylmethoxy group, propoxycarbonylmethoxy group, methoxycarbonylethoxy group, ethoxycarbonylethoxy group, and propoxycarbonylethoxy group; a halogen atom such as fluorine atom, chlorine atom, and bromine atom.

Examples of preferred compounds of the present invention include the compounds of the general formula (I) wherein $R^1$ represents a $C_4$–$C_{10}$ alkyl group, a $C_6$–$C_{10}$ aryl group which may be substituted, a $C_3$–$C_{10}$ cycloalkyl group which may be substituted, or a $C_7$–$C_{12}$ aralkyl group which may be substituted, and $R^3$ represents amidino group. The compounds wherein $R^3$ represents amino group are also preferred.

Examples of more preferred compounds include the compounds of the general formula (I) wherein $R^2$ represents hydrogen atom, a $C_{1-C10}$ alkyl group, a $C_7$–$C_{12}$ aralkyl group which may be substituted, or —$COR^4$ wherein $R^4$ has the same meaning as defined above.

Examples of the most preferred compounds include the compounds of the general formula (I) wherein $R^2$ represents —$COR^4$ in which $R^4$ represents a $C_1$–$C_{10}$ alkyl group, a $C_1$–$C_{10}$ alkoxy group, a $C_6$–$C_{10}$ aryl group which may be substituted, a $C_6$–$C_{10}$ aryloxy group which may be substituted, a $C_3$–$C_{10}$ cycloalkyl group which may be substituted, a $C_3$–$C_{10}$ cycloalkyloxy group which may be substituted, a $C_7$–$C_{12}$ aralkyl group which may be substituted, or a $C_7$–$C_{12}$ aralkyloxy group which may be substituted.

The penicillaminamide derivatives represented by the above general formula (I) may have various stereostructures. For example, in view of an asymmetric carbon atom as an asymmetric center, their absolute configuration may be either in (S) or (R) configuration. they may also exist as racemates. Optical isomers or diastereoisomers in pure forms, or any mixtures of these isomers or racemates fall within the scope of the present invention.

Examples of salts formed by the compounds of the present invention represented by the aforementioned general formula (I) include, for example, inorganic acid salts such as hydrochloride, hydrobromide, hydriodide, sulfate, nitrate, and phosphate, and organic acid salts such as succinate, oxalate, fumarate, maleate, lactate, tartrate, citrate, acetate, glycolate, methanesulfonate, and toluenesulfonate. When the penicillaminamide derivatives of the general formula (I) have a free carboxyl group, they can form salts with pharmaceutically acceptable bases. Examples of the salts include, for example, alkali metal salts, alkaline earth metal salts, ammonium salts, and alkylammonium salts.

The penicillaminamide derivatives represented by the general formula (I) and may form hydrates, or may form solvates with methanol, ethanol, isopropanol, acetone, ethyl acetate, methylene chloride or the like. These substances also fall within the scope of the present invention.

Specific examples of the compounds of the present invention are shown below. In the table, Me represents methyl group, Et represents ethyl group, Ph represents phenyl group, n-Pr represents n-propyl group, i-Pr represents i-propyl group, Bu represents butyl group, n-Bu represents n-butyl group, i-Bu represents i-butyl group, s-bu represents s-butyl group, cyclo-Hex represents cyclohexyl group, 4-F-Benzyl represents 4-fluorobenzyl group, and 4-OMe-Benzyl represents 4-methoxybenzyl group.

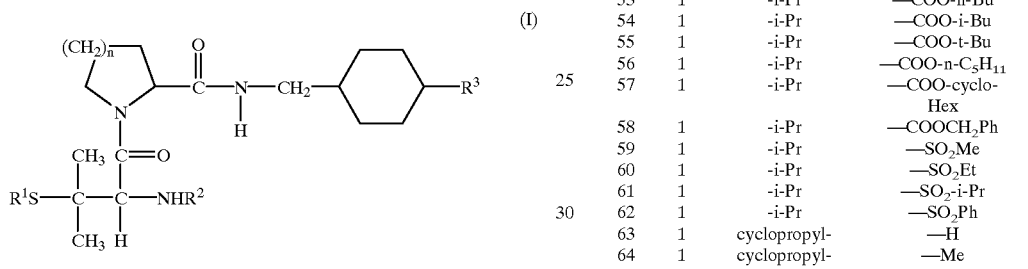

(I)

TABLE 1

| Compound No. | n | R$^1$ | R$^2$ | R$^3$ |
|---|---|---|---|---|
| 1 | 1 | —Me | —H | —NH$_2$ |
| 2 | 1 | —Me | —Me | —NH$_2$ |
| 3 | 1 | —Me | —CH$_2$Ph | —NH$_2$ |
| 4 | 1 | —Me | —COCH$_3$ | —NH$_2$ |
| 5 | 1 | —Me | —COO-n-Pr | —NH$_2$ |
| 6 | 1 | —Me | —COO-i-Pr | —NH$_2$ |
| 7 | 1 | —Me | —SO$_2$Et | —NH$_2$ |
| 8 | 1 | —Et | —H | —NH$_2$ |
| 9 | 1 | —Et | —Me | —NH$_2$ |
| 10 | 1 | —Et | —CH$_2$Ph | —NH$_2$ |
| 11 | 1 | —Et | —COCH$_3$ | —NH$_2$ |
| 12 | 1 | —Et | —COOMe | —NH$_2$ |
| 13 | 1 | —Et | —COOEt | —NH$_2$ |
| 14 | 1 | —Et | —COO-n-Pr | —NH$_2$ |
| 15 | 1 | —Et | —COO-i-Pr | —NH$_2$ |
| 16 | 1 | —Et | —COO-n-Bu | —NH$_2$ |
| 17 | 1 | —Et | —COO-i-Bu | —NH$_2$ |
| 18 | 1 | —Et | —COO-t-Bu | —NH$_2$ |
| 19 | 1 | —Et | —COO-n-C$_5$H$_{11}$ | —NH$_2$ |
| 20 | 1 | —Et | —COOCH$_2$Ph | —NH$_2$ |
| 21 | 1 | —Et | —COO-cyclo-Hex | —NH$_2$ |
| 22 | 1 | —Et | —SO$_2$Et | —NH$_2$ |
| 23 | 1 | —Et | —SO$_2$Me | —NH$_2$ |
| 24 | 1 | -n-Pr | —H | —NH$_2$ |
| 25 | 1 | -n-Pr | —Me | —NH$_2$ |
| 26 | 1 | -n-Pr | —CO$_2$Ph | —NH$_2$ |
| 27 | 1 | -n-Pr | —COCH$_3$ | —NH$_2$ |
| 28 | 1 | -n-Pr— | CO-cyclo-Hex | —NH$_2$ |
| 29 | 1 | -n-Pr | —COPh | —NH$_2$ |
| 30 | 1 | -n-Pr | —COOMe | —NH$_2$ |
| 31 | 1 | -n-Pr | —COOEt | —NH$_2$ |
| 32 | 1 | -n-Pr | —COO-n-Pr | —NH$_2$ |
| 33 | 1 | -n-Pr | —COO-i-Pr | —NH$_2$ |

TABLE 1-continued

| Compound No. | n | R$^1$ | R$^2$ | R$^3$ |
|---|---|---|---|---|
| 34 | 1 | -n-Pr | —COO-n-Bu | —NH$_2$ |
| 35 | 1 | -n-Pr | —COO-i-Bu | —NH$_2$ |
| 36 | 1 | -n-Pr | —COO-t-Bu | —NH$_2$ |
| 37 | 1 | -n-Pr | —COO-n-C$_5$H$_{11}$ | —NH$_2$ |
| 38 | 1 | -n-Pr | —COOCH$_2$Ph | —NH$_2$ |
| 39 | 1 | -n-Pr | —SO$_2$Me | —NH$_2$ |
| 40 | 1 | -n-Pr | —SO$_2$Et | —NH$_2$ |
| 41 | 1 | -n-Pr | —SO$_2$—I—Pr | —NH$_2$ |
| 42 | 1 | -n-Pr | —SO$_2$Ph | —NH$_2$ |
| 43 | 1 | -i-Pr | —H | —NH$_2$ |
| 44 | 1 | -i-Pr | —Me | —NH$_2$ |
| 45 | 1 | -i-Pr | —CH$_2$Ph | —NH$_2$ |
| 46 | 1 | -i-Pr | —COCH$_3$ | —NH$_2$ |
| 47 | 1 | -i-Pr | —CO-cyclo-Hex | —NH$_2$ |
| 48 | 1 | -i-Pr | —COPh | —NH$_2$ |
| 49 | 1 | -i-Pr | —COOMe | —NH$_2$ |
| 50 | 1 | -i-Pr | —COOEt | —NH$_2$ |
| 51 | 1 | -i-Pr | —COO-n-Pr | —NH$_2$ |
| 52 | 1 | -i-Pr | —COO-i-Pr | —NH$_2$ |
| 53 | 1 | -i-Pr | —COO-n-Bu | —NH$_2$ |
| 54 | 1 | -i-Pr | —COO-i-Bu | —NH$_2$ |
| 55 | 1 | -i-Pr | —COO-t-Bu | —NH$_2$ |
| 56 | 1 | -i-Pr | —COO-n-C$_5$H$_{11}$ | —NH$_2$ |
| 57 | 1 | -i-Pr | —COO-cyclo-Hex | —NH$_2$ |
| 58 | 1 | -i-Pr | —COOCH$_2$Ph | —NH$_2$ |
| 59 | 1 | -i-Pr | —SO$_2$Me | —NH$_2$ |
| 60 | 1 | -i-Pr | —SO$_2$Et | —NH$_2$ |
| 61 | 1 | -i-Pr | —SO$_2$-i-Pr | —NH$_2$ |
| 62 | 1 | -i-Pr | —SO$_2$Ph | —NH$_2$ |
| 63 | 1 | cyclopropyl- | —H | —NH$_2$ |
| 64 | 1 | cyclopropyl- | —Me | —NH$_2$ |
| 65 | 1 | cyclopropyl- | —CH$_2$Ph | —NH$_2$ |
| 66 | 1 | cyclopropyl- | —COCH$_3$ | —NH$_2$ |
| 67 | 1 | cyclopropyl- | —SO$_2$Me | —NH$_2$ |
| 68 | 1 | cyclopropyl- | —COOEt | —NH$_2$ |
| 69 | 1 | cyclopropyl- | —COO-i-Pr | —NH$_2$ |
| 70 | 1 | cyclopropyl- | —COOMe | —NH$_2$ |
| 71 | 1 | -n-Bu | —H | —NH$_2$ |
| 72 | 1 | -n-Bu | —Me | —NH$_2$ |
| 73 | 1 | -n-Bu | —CH$_2$Ph | —NH$_2$ |
| 74 | 1 | -n-Bu | —COCH$_3$ | —NH$_2$ |
| 75 | 1 | -n-Bu | —CO-cyclo-Hex | —NH$_2$ |
| 76 | 1 | -n-Bu | —COPh | —NH$_2$ |
| 77 | 1 | -n-Bu | —COOMe | —NH$_2$ |
| 78 | 1 | -n-Bu | —COOEt | —NH$_2$ |
| 79 | 1 | -n-Bu | —COO-n-Pr | —NH$_2$ |
| 80 | 1 | -n-Bu | —COO-i-Pr | —NH$_2$ |
| 81 | 1 | -n-Bu | —COO-n-Bu | —NH$_2$ |
| 82 | 1 | -n-Bu | —COO-i-Bu | —NH$_2$ |
| 83 | 1 | -n-Bu | —COO-t-Bu | —NH$_2$ |
| 84 | 1 | -n-Bu | —COO-n-C$_5$H$_{11}$ | —NH$_2$ |
| 85 | 1 | -n-Bu | —COOCH$_2$Ph | —NH$_2$ |
| 86 | 1 | -n-Bu | —SO$_2$Me | —NH$_2$ |
| 87 | 1 | -n-Bu | —SO$_2$Et | —NH$_2$ |
| 88 | 1 | -n-Bu | —SO$_2$-i-Pr | —NH$_2$ |
| 89 | 1 | -n-Bu | —SO$_2$Ph | —NH$_2$ |
| 90 | 1 | -i-Bu | —H | —NH$_2$ |
| 91 | 1 | -i-Bu | —Me | —NH$_2$ |
| 92 | 1 | -i-Bu | —CH$_2$Ph | —NH$_2$ |
| 93 | 1 | -i-Bu | —COCH$_3$ | —NH$_2$ |
| 94 | 1 | -i-Bu | —CO-cyclo-Hex | —NH$_2$ |
| 95 | 1 | -i-Bu | —COPh | —NH$_2$ |
| 96 | 1 | -i-Bu | —COOMe | —NH$_2$ |
| 97 | 1 | -i-Bu | —COOEt | —NH$_2$ |
| 98 | 1 | -i-Bu | —COO-n-Pr | —NH$_2$ |
| 99 | 1 | -i-Bu | —COO-i-Pr | —NH$_2$ |
| 100 | 1 | -i-Bu | —COO-n-Bu | —NH$_2$ |
| 101 | 1 | -i-Bu | —COO-i-Bu | —NH$_2$ |
| 102 | 1 | -i-Bu | —COO-t-Bu | —NH$_2$ |
| 103 | 1 | -i-Bu | —COO-n-C$_5$H$_{11}$ | —NH$_2$ |
| 104 | 1 | -i-Bu | —COO-cyclo-Hex | —NH$_2$ |
| 105 | 1 | -i-Bu | —COOCH$_2$Ph | —NH$_2$ |
| 106 | 1 | -i-Bu | —SO$_2$Me | —NH$_2$ |

TABLE 1-continued

| Compound No. | n | R$^1$ | R$^2$ | R$^3$ |
|---|---|---|---|---|
| 107 | 1 | -i-Bu | —SO$_2$Et | —NH$_2$ |
| 108 | 1 | -i-Bu | —SO$_2$-i-Pr | —NH$_2$ |
| 109 | 1 | -i-Bu | —SO$_2$Ph | —NH$_2$ |
| 110 | 1 | -s-Bu | —H | —NH$_2$ |
| 111 | 1 | -s-Bu | —Me | —NH$_2$ |
| 112 | 1 | -s-Bu | —CH$_2$Ph | —NH$_2$ |
| 113 | 1 | -s-Bu | —COCH$_3$ | —NH$_2$ |
| 114 | 1 | -s-Bu | —COOMe | —NH$_2$ |
| 115 | 1 | -s-Bu | —COOEt | —NH$_2$ |
| 116 | 1 | -s-Bu | —COO-i-Pr | —NH$_2$ |
| 117 | 1 | -s-Bu | —SO$_2$Me | —NH$_2$ |
| 118 | 1 | -cyclobutyl | —H | —NH$_2$ |
| 119 | 1 | -cyclobutyl | —Me | —NH$_2$ |
| 120 | 1 | -cyclobutyl | —CH$_2$Ph | —NH$_2$ |
| 121 | 1 | -cyclobutyl | —COCH$_3$ | —NH$_2$ |
| 122 | 1 | -cyclobutyl | —CO-cyclo-Hex | —NH$_2$ |
| 123 | 1 | -cyclobutyl | —COPh | —NH$_2$ |
| 124 | 1 | -cyclobutyl | —COOMe | —NH$_2$ |
| 125 | 1 | -cyclobutyl | —COOEt | —NH$_2$ |
| 126 | 1 | -cyclobutyl | —COO-n-Pr | —NH$_2$ |
| 127 | 1 | -cyclobutyl | —COO-i-Pr | —NH$_2$ |
| 128 | 1 | -cyclobutyl | —COO-n-Bu | —NH$_2$ |
| 129 | 1 | -cyclobutyl | —COO-i-Bu | —NH$_2$ |
| 130 | 1 | -cyclobutyl | —COO-t-Bu | —NH$_2$ |
| 131 | 1 | -cyclobutyl | —COO-n-C$_5$H$_{11}$ | —NH$_2$ |
| 132 | 1 | -cyclobutyl | —COO-cyclo-Hex | —NH$_2$ |
| 133 | 1 | -cyclobutyl | —COOCH$_2$Ph | —NH$_2$ |
| 134 | 1 | -cyclobutyl | —SO$_2$Me | —NH$_2$ |
| 135 | 1 | -cyclobutyl | —SO$_2$Et | —NH$_2$ |
| 136 | 1 | -cyclobutyl | —SO$_2$-i-Pr | —NH$_2$ |
| 137 | 1 | -cyclobutyl | —SO$_2$Ph | —NH$_2$ |
| 138 | 1 | -n-C$_5$H$_{11}$ | —H | —NH$_2$ |
| 139 | 1 | -n-C$_5$H$_{11}$ | —Me | —NH$_2$ |
| 140 | 1 | -n-C$_5$H$_{11}$ | —CH$_2$Ph | —NH$_2$ |
| 141 | 1 | -n-C$_5$H$_{11}$ | —COCH$_3$ | —NH$_2$ |
| 142 | 1 | -n-C$_5$H$_{11}$ | —CO-cyclo-Hex | —NH$_2$ |
| 143 | 1 | -n-C$_5$H$_{11}$ | —COPh | —NH$_2$ |
| 144 | 1 | -n-C$_5$H$_{11}$ | —COOMe | —NH$_2$ |
| 145 | 1 | -n-C$_5$H$_{11}$ | —COOEt | —NH$_2$ |
| 146 | 1 | -n-C$_5$H$_{11}$ | —COO-n-Pr | —NH$_2$ |
| 147 | 1 | -n-C$_5$H$_{11}$ | —COO-i-Pr | —NH$_2$ |
| 148 | 1 | -n-C$_5$H$_{11}$ | —COO-n-Bu | —NH$_2$ |
| 149 | 1 | -n-C$_5$H$_{11}$ | —COO-i-Bu | —NH$_2$ |
| 150 | 1 | -n-C$_5$H$_{11}$ | —COO-t-Bu | —NH$_2$ |
| 151 | 1 | -n-C$_5$H$_{11}$ | —COO-n-C$_5$H$_{11}$ | —NH$_2$ |
| 152 | 1 | -n-C$_5$H$_{11}$ | —COOCH$_2$Ph | —NH$_2$ |
| 153 | 1 | -n-C$_5$H$_{11}$ | —SO$_2$Me | —NH$_2$ |
| 154 | 1 | -n-C$_5$H$_{11}$ | —SO$_2$Et | —NH$_2$ |
| 155 | 1 | -n-C$_5$H$_{11}$ | —SO$_2$-i-Pr | —NH$_2$ |
| 156 | 1 | -n-C$_5$H$_{11}$ | —SO$_2$Ph | —NH$_2$ |
| 157 | 1 | -cyclopentyl | —H | —NH$_2$ |
| 158 | 1 | -cyclopentyl | —Me | —NH$_2$ |
| 159 | 1 | -cyclopentyl | —CH$_2$Ph | —NH$_2$ |
| 160 | 1 | -cyclopentyl | —COCH$_3$ | —NH$_2$ |
| 161 | 1 | -cyclopentyl | —CO-cyclo-Hex | —NH$_2$ |
| 162 | 1 | -cyclopentyl | —COPh | —NH$_2$ |
| 163 | 1 | -cyclopentyl | —COOMe | —NH$_2$ |
| 164 | 1 | -cyclopentyl | —COOEt | —NH$_2$ |
| 165 | 1 | -cyclopentyl | —COO-n-Pr | —NH$_2$ |
| 166 | 1 | -cyclopentyl | —COO-n-Bu | —NH$_2$ |
| 167 | 1 | -cyclopentyl | —COO-i-Bu | —NH$_2$ |
| 168 | 1 | -cyclopentyl | —COO-t-Bu | —NH$_2$ |
| 169 | 1 | -cyclopentyl | —COO-n-C$_5$H$_{11}$ | —NH$_2$ |
| 170 | 1 | -cyclopentyl | —SO$_2$Me | —NH$_2$ |
| 171 | 1 | -cyclopentyl | —SO$_2$Et | —NH$_2$ |
| 172 | 1 | -cyclopentyl | —SO$_2$-i-Pr | —NH$_2$ |
| 173 | 1 | -cyclopentyl | —SO$_2$Ph | —NH$_2$ |
| 174 | 1 | —CH(CH$_2$CH$_3$)$_2$ | —H | —NH$_2$ |
| 175 | 1 | —CH(CH$_2$CH$_3$)$_2$ | —Me | —NH$_2$ |
| 176 | 1 | —CH(CH$_2$CH$_3$)$_2$ | —CH$_2$Ph | —NH$_2$ |
| 177 | 1 | —CH(CH$_2$CH$_3$)$_2$ | —COCH$_3$ | —NH$_2$ |
| 178 | 1 | —CH(CH$_2$CH$_3$)$_2$ | —CO-cyclo-Hex | —NH$_2$ |
| 179 | 1 | —CH(CH$_2$CH$_3$)$_2$ | —COPh | —NH$_2$ |
| 180 | 1 | —CH(CH$_2$CH$_3$)$_2$ | —COOMe | —NH$_2$ |
| 181 | 1 | —CH(CH$_2$CH$_3$)$_2$ | —COOEt | —NH$_2$ |
| 182 | 1 | —CH(CH$_2$CH$_3$)$_2$ | —COO-n-Pr | —NH$_2$ |
| 183 | 1 | —CH(CH$_2$CH$_3$)$_2$ | —COO-i-Pr | —NH$_2$ |
| 184 | 1 | —CH(CH$_2$CH$_3$)$_2$ | —COO-n-Bu | —NH$_2$ |
| 185 | 1 | —CH(CH$_2$CH$_3$)$_2$ | —COO-i-Bu | —NH$_2$ |
| 186 | 1 | —CH(CH$_2$CH$_3$)$_2$ | —COO-t-Bu | —NH$_2$ |
| 187 | 1 | —CH(CH$_2$CH$_3$)$_2$ | —COO-n-C$_5$H$_{11}$ | —NH$_2$ |
| 188 | 1 | —CH(CH$_2$CH$_3$)$_2$ | —SO$_2$Me | —NH$_2$ |
| 189 | 1 | —CH(CH$_2$CH$_3$)$_2$ | —SO$_2$Et | —NH$_2$ |
| 190 | 1 | —CH(CH$_2$CH$_3$)$_2$ | —SO$_2$-i-Pr | —NH$_2$ |
| 191 | 1 | —CH(CH$_2$CH$_3$)$_2$ | —SO$_2$Ph | —NH$_2$ |
| 192 | 1 | -cyclohexyl | —H | —NH$_2$ |
| 193 | 1 | -cyclohexyl | —Me | —NH$_2$ |
| 194 | 1 | -cyclohexyl | —CH$_2$Ph | —NH$_2$ |
| 195 | 1 | -cyclohexyl | —COCH$_3$ | —NH$_2$ |
| 196 | 1 | -cyclohexyl | —COOMe | —NH$_2$ |
| 197 | 1 | -cyclohexyl | —COOEt | —NH$_2$ |
| 198 | 1 | -cyclohexyl | —COO-i-Pr | —NH$_2$ |
| 199 | 1 | -cyclohexyl | —SO$_2$Me | —NH$_2$ |
| 200 | 1 | -cyclohexyl | —SO$_2$-i-Pr | —NH$_2$ |
| 201 | 1 | —Ph | —H | —NH$_2$ |
| 202 | 1 | —Ph | —Me | —NH$_2$ |
| 203 | 1 | —Ph | —CH$_2$Ph | —NH$_2$ |
| 204 | 1 | —Ph | —COCH$_3$ | —NH$_2$ |
| 205 | 1 | —Ph | —COOMe | —NH$_2$ |
| 206 | 1 | —Ph | —COOEt | —NH$_2$ |
| 207 | 1 | —Ph | —COO-i-Pr | —NH$_2$ |
| 208 | 1 | —Ph | —SO$_2$Me | —NH$_2$ |
| 209 | 1 | —Ph | —SO$_2$-i-Pr | —NH$_2$ |
| 210 | 1 | -Benzyl | —H | —NH$_2$ |
| 211 | 1 | -Benzyl | —Me | —NH$_2$ |
| 212 | 1 | -Benzyl | —CH$_2$Ph | —NH$_2$ |
| 213 | 1 | -Benzyl | —COCH$_3$ | —NH$_2$ |
| 214 | 1 | -Benzyl | —COOEt | —NH$_2$ |
| 215 | 1 | -Benzyl | —COO-n-Pr | —NH$_2$ |
| 216 | 1 | -Benzyl | —COO-i-Pr | —NH$_2$ |
| 217 | 1 | -Benzyl | —SO$_2$Me | —NH$_2$ |
| 218 | 1 | 4-F-Benzyl- | —H | —NH$_2$ |
| 219 | 1 | 4-F-Benzyl- | —Me | —NH$_2$ |
| 220 | 1 | 4-F-Benzyl- | —CH$_2$Ph | —NH$_2$ |
| 221 | 1 | 4-F-Benzyl- | —COCH$_3$ | —NH$_2$ |
| 222 | 1 | 4-F-Benzyl- | —COOMe | —NH$_2$ |
| 223 | 1 | 4-F-Benzyl- | —COOEt | —NH$_2$ |
| 224 | 1 | 4-F-Benzyl- | —COO-i-Pr | —NH$_2$ |
| 225 | 1 | 4-F-Benzyl- | —SO$_2$Me | —NH$_2$ |
| 226 | 1 | 4-OMe-Benzyl- | —H | —NH$_2$ |
| 227 | 1 | 4-OMe-Benzyl- | —Me | —NH$_2$ |
| 228 | 1 | 4-OMe-Benzyl- | —CH$_2$Ph | —NH$_2$ |
| 229 | 1 | 4-OMe-Benzyl- | —COCH$_3$ | —NH$_2$ |
| 230 | 1 | 4-OMe-Benzyl- | —COOMe | —NH$_2$ |
| 231 | 1 | 4-OMe-Benzyl- | —COOEt | —NH$_2$ |
| 232 | 1 | 4-OMe-Benzyl- | —COO-i-Pr | —NH$_2$ |
| 233 | 1 | 4-OMe-Benzyl- | —SO$_2$Me | —NH$_2$ |
| 234 | 1 | —CH$_2$-cyclo-Hex | —H | —NH$_2$ |
| 235 | 1 | —CH$_2$-cyclo-Hex | —Me | —NH$_2$ |
| 236 | 1 | —CH$_2$-cyclo-Hex | —CH$_2$Ph | —NH$_2$ |
| 237 | 1 | —CH$_2$-cyclo-Hex | —COCH$_3$ | —NH$_2$ |
| 238 | 1 | —CH$_2$-cyclo-Hex | —COOMe | —NH$_2$ |
| 239 | 1 | —CH$_2$-cyclo-Hex | —COOEt | —NH$_2$ |
| 240 | 1 | —CH$_2$-cyclo-Hex | —COO-i-Pr | —NH$_2$ |
| 241 | 1 | —CH$_2$-cyclo-Hex | —COO-n-Pr | —NH$_2$ |
| 242 | 1 | —CH$_2$-cyclo-Hex | —SO$_2$Me | —NH$_2$ |
| 243 | 1 | —CH$_2$C(CH$_3$)$_3$ | —H | —NH$_2$ |
| 244 | 1 | —CH$_2$C(CH$_3$)$_3$ | —Me | —NH$_2$ |
| 245 | 1 | —CH$_2$C(CH$_3$)$_3$ | —CH$_2$Ph | —NH$_2$ |
| 246 | 1 | —CH$_2$C(CH$_3$)$_3$ | —COCH$_3$ | —NH$_2$ |
| 247 | 1 | —CH$_2$C(CH$_3$)$_3$ | —COOEt | —NH$_2$ |
| 248 | 1 | —CH$_2$C(CH$_3$)$_3$ | —COO-n-Pr | —NH$_2$ |
| 249 | 1 | —CH$_2$C(CH$_3$)$_3$ | —COO-i-Pr | —NH$_2$ |
| 250 | 1 | —CH$_2$C(CH$_3$)$_3$ | —SO$_2$Me | —NH$_2$ |
| 251 | 1 | —(CH$_2$)$_2$CH(CH$_3$)$_2$ | —H | —NH$_2$ |
| 252 | 1 | —(CH$_2$)$_2$CH(CH$_3$)$_2$ | —Me | —NH$_2$ |
| 253 | 1 | —(CH$_2$)$_2$CH(CH$_3$)$_2$ | —COCH$_3$ | —NH$_2$ |
| 254 | 1 | —(CH$_2$)$_2$CH(CH$_3$)$_2$ | —COOEt | —NH$_2$ |
| 255 | 1 | —(CH$_2$)$_2$CH(CH$_3$)$_2$ | —COO-n-Pr | —NH$_2$ |

TABLE 1-continued

| Compound No. | n | R¹ | R² | R³ |
|---|---|---|---|---|
| 256 | 1 | —(CH₂)₂CH(CH₃)₂ | —COO-i-Pr | —NH₂ |
| 257 | 1 | —(CH₂)₂CH(CH₃)₂ | —SO₂Me | —NH₂ |
| 258 | 2 | —Me | —H | —NH₂ |
| 259 | 2 | —Me | —Me | —NH₂ |
| 260 | 2 | —Me | —COCH₃ | —NH₂ |
| 261 | 2 | —Me | —COOMe | —NH₂ |
| 262 | 2 | —Me | —COOEt | —NH₂ |
| 263 | 2 | —Me | —COO-i-Pr | —NH₂ |
| 264 | 2 | —Me | —SO₂Me | —NH₂ |
| 265 | 2 | —Et | —H | —NH₂ |
| 266 | 2 | —Et | —Me | —NH₂ |
| 267 | 2 | —Et | —COCH₃ | —NH₂ |
| 268 | 2 | —Et | —COOMe | —NH₂ |
| 269 | 2 | —Et | —COOEt | —NH₂ |
| 270 | 2 | —Et | —COO-n-Pr | —NH₂ |
| 271 | 2 | —Et | —COO-i-Pr | —NH₂ |
| 272 | 2 | —Et | —COO-n-Bu | —NH₂ |
| 273 | 2 | —Et | —COO-i-Bu | —NH₂ |
| 274 | 2 | —Et | —COO-t-Bu | —NH₂ |
| 275 | 2 | —Et | —SO₂Me | —NH₂ |
| 276 | 2 | -n-Pr | —H | —NH₂ |
| 277 | 2 | -n-Pr | —Me | —NH₂ |
| 278 | 2 | -n-Pr | —COCH₃ | —NH₂ |
| 279 | 2 | -n-Pr | —COOMe | —NH₂ |
| 280 | 2 | -n-Pr | —COOEt | —NH₂ |
| 281 | 2 | -n-Pr | —COO-n-Pr | —NH₂ |
| 282 | 2 | -n-Pr | —COO-i-Pr | —NH₂ |
| 283 | 2 | -n-Pr | —COO-n-Bu | —NH₂ |
| 284 | 2 | -n-Pr | —COO-t-Bu | —NH₂ |
| 285 | 2 | -n-Pr | —COO-i-Bu | —NH₂ |
| 286 | 2 | -n-Pr | —SO₂Me | —NH₂ |
| 287 | 2 | -i-Pr | —H | —NH₂ |
| 288 | 2 | -i-Pr | —Me | —NH₂ |
| 289 | 2 | -i-Pr | —COCH₃ | —NH₂ |
| 290 | 2 | -i-Pr | —COOMe | —NH₂ |
| 291 | 2 | -i-Pr | —COOEt | —NH₂ |
| 292 | 2 | -i-Pr | —COO-n-Pr | —NH₂ |
| 293 | 2 | -i-Pr | —COO-i-Pr | —NH₂ |
| 294 | 2 | -i-Pr | —COO-n-Bu | —NH₂ |
| 295 | 2 | -i-Pr | —COO-i-Bu | —NH₂ |
| 296 | 2 | -i-Pr | —COO-t-Bu | —NH₂ |
| 297 | 2 | -i-Pr | —SO₂Me | —NH₂ |
| 298 | 2 | -n-Bu | —H | —NH₂ |
| 299 | 2 | -n-Bu | —Me | —NH₂ |
| 300 | 2 | -n-Bu | —COCH₃ | —NH₂ |
| 301 | 2 | -n-Bu | —COOMe | —NH₂ |
| 302 | 2 | -n-Bu | —COOEt | —NH₂ |
| 303 | 2 | -n-Bu | —COO-n-Pr | —NH₂ |
| 304 | 2 | -n-Bu | —COO-i-Pr | —NH₂ |
| 305 | 2 | -n-Bu | —COO-n-Bu | —NH₂ |
| 306 | 2 | -n-Bu | —COO-i-Bu | —NH₂ |
| 307 | 2 | -n-Bu | —COO-t-Bu | —NH₂ |
| 308 | 2 | -n-Bu | —SO₂Me | —NH₂ |
| 309 | 2 | -i-Bu | —H | —NH₂ |
| 310 | 2 | -i-Bu | —Me | —NH₂ |
| 311 | 2 | -i-Bu | —COCH₃ | —NH₂ |
| 312 | 2 | -i-Bu | —COOMe | —NH₂ |
| 313 | 2 | -i-Bu | —COOEt | —NH₂ |
| 314 | 2 | -i-Bu | —COO-n-Pr | —NH₂ |
| 315 | 2 | -i-Bu | —COO-i-Pr | —NH₂ |
| 316 | 2 | -i-Bu | —COO-n-Bu | —NH₂ |
| 317 | 2 | -i-Bu | —COO-i-Bu | —NH₂ |
| 318 | 2 | -i-Bu | —COO-t-Bu | —NH₂ |
| 319 | 2 | -i-Bu | —SO₂Me | —NH₂ |
| 320 | 2 | -cyclobutyl | —H | —NH₂ |
| 321 | 2 | -cyclobutyl | —Me | —NH₂ |
| 322 | 2 | -cyclobutyl | —COCH₃ | —NH₂ |
| 323 | 2 | -cyclobutyl | —COOMe | —NH₂ |
| 324 | 2 | -cyclobutyl | —COOEt | —NH₂ |
| 325 | 2 | -cyclobutyl | —COO-n-Pr | —NH₂ |
| 326 | 2 | -cyclobutyl | —COO-i-Pr | —NH₂ |
| 327 | 2 | -cyclobutyl | —COO-t-Bu | —NH₂ |
| 328 | 2 | -cyclobutyl | —SO₂Me | —NH₂ |
| 329 | 2 | -cyclopentyl | —H | —NH₂ |
| 330 | 2 | -cyclopentyl | —Me | —NH₂ |
| 331 | 2 | -cyclopentyl | —COCH₃ | —NH₂ |
| 332 | 2 | -cyclopentyl | —COOMe | —NH₂ |
| 333 | 2 | -cyclopentyl | —COOEt | —NH₂ |
| 334 | 2 | -cyclopentyl | —COO-n-Pr | —NH₂ |
| 335 | 2 | -cyclopentyl | —COO-i-Pr | —NH₂ |
| 336 | 2 | -cyclopentyl | —COO-t-Bu | —NH₂ |
| 337 | 2 | -Benzyl | —H | —NH₂ |
| 338 | 2 | -Benzyl | —Me | —NH₂ |
| 339 | 2 | -Benzyl | —COCH₃ | —NH₂ |
| 340 | 2 | -Benzyl | —COOMe | —NH₂ |
| 341 | 2 | -Benzyl | —COOEt | —NH₂ |
| 342 | 2 | -Benzyl | —COO-n-Pr | —NH₂ |
| 343 | 2 | -Benzyl | —COO-i-Pr | —NH₂ |
| 344 | 2 | -Benzyl | —COO-t-Bu | —NH₂ |
| 345 | 2 | -Benzyl | —SO₂Me | —NH₂ |
| 346 | 2 | —CH₂C(CH₃)₃ | —H | —NH₂ |
| 347 | 2 | —CH₂C(CH₃)₃ | —Me | —NH₂ |
| 348 | 2 | —CH₂C(CH₃)₃ | —COCH₃ | —NH₂ |
| 349 | 2 | —CH₂C(CH₃)₃ | —COOMe | —NH₂ |
| 350 | 2 | —CH₂C(CH₃)₃ | —COOEt | —NH₂ |
| 351 | 2 | —CH₂C(CH₃)₃ | —COO-n-Pr | —NH₂ |
| 352 | 2 | —CH₂C(CH₃)₃ | —COO-i-Pr | —NH₂ |
| 353 | 2 | —CH₂C(CH₃)₃ | COO-t-Bu | —NH₂ |
| 354 | 2 | —CH₂C(CH₃)₃ | —SO₂Me | —NH₂ |
| 355 | 2 | —CH(CH₂CH₃)₂ | —H | —NH₂ |
| 356 | 2 | —CH(CH₂CH₃)₂ | —Me | —NH₂ |
| 357 | 2 | —CH(CH₂CH₃)₂ | —COCH₃ | —NH₂ |
| 358 | 2 | —CH(CH₂CH₃)₂ | —COOMe | —NH₂ |
| 359 | 2 | —CH(CH₂CH₃)₂ | —COOEt | —NH₂ |
| 360 | 2 | —CH(CH₂CH₃)₂ | —COO-n-Pr | —NH₂ |
| 361 | 2 | —CH(CH₂CH₃)₂ | —COO-i-Pr | —NH₂ |
| 362 | 2 | —CH(CH₂CH₃)₂ | —COO-t-Bu | —NH₂ |
| 363 | 2 | —CH(CH₂CH₃)₂ | —SO₂Me | —NH₂ |
| 364 | 1 | —Me | —H | —C(NH₂)=NH |
| 365 | 1 | —Me | —Me | —C(NH₂)=NH |
| 366 | 1 | —Me | —CH₂Ph | —C(NH₂)=NH |
| 367 | 1 | —Me | —COCH₃ | —C(NH₂)=NH |
| 368 | 1 | —Me | —COO-n-Pr | —C(NH₂)=NH |
| 369 | 1 | —Me | —COO-i-Pr | —C(NH₂)=NH |
| 370 | 1 | —Me | —SO₂Me | —C(NH₂)=NH |
| 371 | 1 | —Et | —H | —C(NH₂)=NH |
| 372 | 1 | —Et | —Me | —C(NH₂)=NH |
| 373 | 1 | —Et | —CH₂Ph | —C(NH₂)=NH |
| 374 | 1 | —Et | —COCH₃ | —C(NH₂)=NH |
| 375 | 1 | —Et | —COOMe | —C(NH₂)=NH |
| 376 | 1 | —Et | —COOEt | —C(NH₂)=NH |
| 377 | 1 | —Et | —COO-n-Pr | —C(NH₂)=NH |
| 378 | 1 | —Et | —COO-i-Pr | —C(NH₂)=NH |
| 379 | 1 | —Et | —COO-n-Bu | —C(NH₂)=NH |
| 380 | 1 | —Et | —COO-i-Bu | —C(NH₂)=NH |
| 381 | 1 | —Et | —COO-t-Bu | —C(NH₂)=NH |
| 382 | 1 | —Et | —COO-n-C₅H₁₁ | —C(NH₂)=NH |
| 383 | 1 | —Et | —COOCH₂Ph | —C(NH₂)=NH |
| 384 | 1 | —Et | —SO₂Me | —C(NH₂)=NH |
| 385 | 1 | —Et | —SO₂Et | —C(NH₂)=NH |
| 386 | 1 | —Et | —SO₂-i-Pr | —C(NH₂)=NH |
| 387 | 1 | -n-Pr | —H | —C(NH₂)=NH |
| 388 | 1 | -n-Pr | —Me | —C(NH₂)=NH |
| 389 | 1 | -n-Pr | —CH₂Ph | —C(NH₂)=NH |
| 390 | 1 | -n-Pr | —COCH₃ | —C(NH₂)=NH |
| 391 | 1 | -n-Pr | —COPh | —C(NH₂)=NH |
| 392 | 1 | -n-Pr | —COOMe | —C(NH₂)=NH |
| 393 | 1 | -n-Pr | —COOEt | —C(NH₂)=NH |
| 394 | 1 | -n-Pr | —COO-n-Pr | —C(NH₂)=NH |
| 395 | 1 | -n-Pr | —COO-i-Pr | —C(NH₂)=NH |
| 396 | 1 | -n-Pr | —COO-n-Bu | —C(NH₂)=NH |
| 397 | 1 | -n-Pr | —COO-i-Bu | —C(NH₂)=NH |
| 398 | 1 | -n-Pr | —COO-t-Bu | —C(NH₂)=NH |
| 399 | 1 | -n-Pr | —COO-n-C₅H₁₁ | —C(NH₂)=NH |
| 400 | 1 | -n-Pr | —COOCH₂Ph | —C(NH₂)=NH |
| 401 | 1 | -n-Pr | —SO₂Me | —C(NH₂)=NH |
| 402 | 1 | -n-Pr | —SO₂Et | —C(NH₂)=NH |
| 403 | 1 | -n-Pr | —SO₂-i-Pr | —C(NH₂)=NH |
| 404 | 1 | -n-Pr | —SO₂Ph | —C(NH₂)=NH |
| 405 | 1 | -i-Pr | —H | —C(NH₂)=NH |

TABLE 1-continued

| Compound No. | n | R¹ | R² | R³ |
|---|---|---|---|---|
| 406 | 1 | -i-Pr | —Me | —C(NH₂)=NH |
| 407 | 1 | -i-Pr | —CH₂Ph | —C(NH₂)=NH |
| 408 | 1 | -i-Pr | —COCH₃ | —C(NH₂)=NH |
| 409 | 1 | -i-Pr | —COPh | —C(NH₂)=NH |
| 410 | 1 | -i-Pr | —COO-n-Pr | —C(NH₂)=NH |
| 411 | 1 | -i-Pr | —COO-i-Pr | —C(NH₂)=NH |
| 412 | 1 | -i-Pr | —COO-n-Bu | —C(NH₂)=NH |
| 413 | 1 | -i-Pr | —COO-i-Bu | —C(NH₂)=NH |
| 414 | 1 | -i-Pr | —COO-t-Bu | —C(NH₂)=NH |
| 415 | 1 | -i-Pr | —COO-n-C₅H₁₁ | —C(NH₂)=NH |
| 416 | 1 | -i-Pr | —COOCH₂Ph | —C(NH₂)=NH |
| 417 | 1 | -i-Pr | —SO₂Me | —C(NH₂)=NH |
| 418 | 1 | -i-Pr | —SO₂Et | —C(NH₂)=NH |
| 419 | 1 | -i-Pr | —COOMe | —C(NH₂)=NH |
| 420 | 1 | -i-Pr | —SO₂Ph | —C(NH₂)=NH |
| 421 | 1 | cyclopropyl- | —H | —C(NH₂)=NH |
| 422 | 1 | cyclopropyl- | —Me | —C(NH₂)=NH |
| 423 | 1 | cyclopropyl- | —COCH₃ | —C(NH₂)=NH |
| 424 | 1 | cyclopropyl- | —SO₂Me | —C(NH₂)=NH |
| 425 | 1 | cyclopropyl- | —COOEt | —C(NH₂)=NH |
| 426 | 1 | cyclopropyl- | —COOMe | —C(NH₂)=NH |
| 427 | 1 | cyclopropyl- | —COO-i-Pr | —C(NH₂)=NH |
| 428 | 1 | -n-Bu | —H | —C(NH₂)=NH |
| 429 | 1 | -n-Bu | —Me | —C(NH₂)=NH |
| 430 | 1 | -n-Bu | —CH₂Ph | —C(NH₂)=NH |
| 431 | 1 | -n-Bu | —COCH₃ | —C(NH₂)=NH |
| 432 | 1 | -n-Bu | —COPh | —C(NH₂)=NH |
| 433 | 1 | -n-Bu | —COOMe | —C(NH₂)=NH |
| 434 | 1 | -n-Bu | —COOEt | —C(NH₂)=NH |
| 435 | 1 | -n-Bu | —COO-n-Pr | —C(NH₂)=NH |
| 436 | 1 | -n-Bu | —COO-i-Pr | —C(NH₂)=NH |
| 437 | 1 | -n-Bu | —COO-n-Bu | —C(NH₂)=NH |
| 438 | 1 | -n-Bu | —COO-i-Bu | —C(NH₂)=NH |
| 439 | 1 | -n-Bu | —COO-t-Bu | —C(NH₂)=NH |
| 440 | 1 | -n-Bu | —COO-n-C₅H₁₁ | —C(NH₂)=NH |
| 441 | 1 | -n-Bu | —COOCH₂Ph | —C(NH₂)=NH |
| 442 | 1 | -n-Bu | —SO₂Me | —C(NH₂)=NH |
| 443 | 1 | -n-Bu | —SO₂Et | —C(NH₂)=NH |
| 444 | 1 | -n-Bu | —SO₂-i-Pr | —C(NH₂)=NH |
| 445 | 1 | -n-Bu | —SO₂Ph | —C(NH₂)=NH |
| 446 | 1 | -i-Bu | —H | —C(NH₂)=NH |
| 447 | 1 | -i-Bu | —Me | —C(NH₂)=NH |
| 448 | 1 | -i-Bu | —CH₂Ph | —C(NH₂)=NH |
| 449 | 1 | -i-Bu | —COCH₃ | —C(NH₂)=NH |
| 450 | 1 | -i-Bu | —COPh | —C(NH₂)=NH |
| 451 | 1 | -i-Bu | —COOMe | —C(NH₂)=NH |
| 452 | 1 | -i-Bu | —COOEt | —C(NH₂)=NH |
| 453 | 1 | -i-Bu | —COO-n-Pr | —C(NH₂)=NH |
| 454 | 1 | -i-Bu | —COO-i-Pr | —C(NH₂)=NH |
| 455 | 1 | -i-Bu | —COO-n-Bu | —C(NH₂)=NH |
| 456 | 1 | -i-Bu | —COO-i-Bu | —C(NH₂)=NH |
| 457 | 1 | -i-Bu | —COO-t-Bu | —C(NH₂)=NH |
| 458 | 1 | -i-Bu | —COO-n-C₅H₁₁ | —C(NH₂)=NH |
| 459 | 1 | -i-Bu | —COOCH₂Ph | —C(NH₂)=NH |
| 460 | 1 | -i-Bu | —SO₂Me | —C(NH₂)=NH |
| 461 | 1 | -i-Bu | —SO₂Et | —C(NH₂)=NH |
| 462 | 1 | -i-Bu | —SO₂-i-Pr | —C(NH₂)=NH |
| 463 | 1 | -i-Bu | —SO₂Ph | —C(NH₂)=NH |
| 464 | 1 | -cyclobutyl | —H | —C(NH₂)=NH |
| 465 | 1 | -cyclobutyl | —Me | —C(NH₂)=NH |
| 466 | 1 | -cyclobutyl | —COCH₃ | —C(NH₂)=NH |
| 467 | 1 | -cyclobutyl | —COOMe | —C(NH₂)=NH |
| 468 | 1 | -cyclobutyl | —COOEt | —C(NH₂)=NH |
| 469 | 1 | -cyclobutyl | —COO-n-Pr | —C(NH₂)=NH |
| 470 | 1 | -cyclobutyl | —COO-i-Pr | —C(NH₂)=NH |
| 471 | 1 | -cyclobutyl | —COO-n-Bu | —C(NH₂)=NH |
| 472 | 1 | -cyclobutyl | —COO-i-Bu | —C(NH₂)=NH |
| 473 | 1 | -cyclobutyl | —COO-t-Bu | —C(NH₂)=NH |
| 474 | 1 | -cyclobutyl | —COO-n-C₅H₁₁ | —C(NH₂)=NH |
| 475 | 1 | -cyclobutyl | —COOCH₂Ph | —C(NH₂)=NH |
| 476 | 1 | -cyclobutyl | —SO₂Me | —C(NH₂)=NH |
| 477 | 1 | -cyclobutyl | —SO₂-i-Pr | —C(NH₂)=NH |
| 478 | 1 | -cyclobutyl | —SO₂Ph | —C(NH₂)=NH |
| 479 | 1 | -n-C₅H₁₁ | —H | —C(NH₂)=NH |
| 480 | 1 | -n-C₅H₁₁ | —Me | —C(NH₂)=NH |
| 481 | 1 | -n-C₅H₁₁ | —COCH₃ | —C(NH₂)=NH |
| 482 | 1 | -n-C₅H₁₁ | —COOMe | —C(NH₂)=NH |
| 483 | 1 | -n-C₅H₁₁ | —COOEt | —C(NH₂)=NH |
| 484 | 1 | -n-C₅H₁₁ | —COO-n-Pr | —C(NH₂)=NH |
| 485 | 1 | -n-C₅H₁₁ | —COO-i-Pr | —C(NH₂)=NH |
| 486 | 1 | -n-C₅H₁₁ | —COO-n-Bu | —C(NH₂)=NH |
| 487 | 1 | -n-C₅H₁₁ | —COO-i-Bu | —C(NH₂)=NH |
| 488 | 1 | -n-C₅H₁₁ | —COO-t-Bu | —C(NH₂)=NH |
| 489 | 1 | -n-C₅H₁₁ | —COO-n-C₅H₁₁ | —C(NH₂)=NH |
| 490 | 1 | -n-C₅H₁₁ | —COOCH₂Ph | —C(NH₂)=NH |
| 491 | 1 | -n-C₅H₁₁ | —SO₂Me | —C(NH₂)=NH |
| 492 | 1 | -n-C₅H₁₁ | —SO₂Et | —C(NH₂)=NH |
| 493 | 1 | -n-C₅H₁₁ | —SO₂-i-Pr | —C(NH₂)=NH |
| 494 | 1 | -n-C₅H₁₁ | —SO₂Ph | —C(NH₂)=NH |
| 495 | 1 | -cyclopentyl | —H | —C(NH₂)=NH |
| 496 | 1 | -cyclopentyl | —Me | —C(NH₂)=NH |
| 497 | 1 | -cyclopentyl | —COCH₃ | —C(NH₂)=NH |
| 498 | 1 | -cyclopentyl | —COOMe | —C(NH₂)=NH |
| 499 | 1 | -cyclopentyl | —COOEt | —C(NH₂)=NH |
| 500 | 1 | -cyclopentyl | —COO-n-Pr | —C(NH₂)=NH |
| 501 | 1 | -cyclopentyl | —COO-i-Pr | —C(NH₂)=NH |
| 502 | 1 | -cyclopentyl | —COO-n-Bu | —C(NH₂)=NH |
| 503 | 1 | -cyclopentyl | —COO-i-Bu | —C(NH₂)=NH |
| 504 | 1 | -cyclopentyl | —COO-t-Bu | —C(NH₂)=NH |
| 505 | 1 | -cyclopentyl | —COO-n-C₅H₁₁ | —C(NH₂)=NH |
| 506 | 1 | -cyclopentyl | —SO₂Me | —C(NH₂)=NH |
| 507 | 1 | -cyclopentyl | —SO₂Et | —C(NH₂)=NH |
| 508 | 1 | -cyclopentyl | —SO₂-i-Pr | —C(NH₂)=NH |
| 509 | 1 | -cyclopentyl | —SO₂Ph | —C(NH₂)=NH |
| 510 | 1 | —CH(CH₂CH₃)₂ | —H | —C(NH₂)=NH |
| 511 | 1 | —CH(CH₂CH₃)₂ | —Me | —C(NH₂)=NH |
| 512 | 1 | —CH(CH₂CH₃)₂ | —COCH₃ | —C(NH₂)=NH |
| 513 | 1 | —CH(CH₂CH₃)₂ | —COOMe | —C(NH₂)=NH |
| 514 | 1 | —CH(CH₂CH₃)₂ | —COOEt | —C(NH₂)=NH |
| 515 | 1 | —CH(CH₂CH₃)₂ | —COO-n-Pr | —C(NH₂)=NH |
| 516 | 1 | —CH(CH₂CH₃)₂ | —COO-i-Pr | —C(NH₂)=NH |
| 517 | 1 | —CH(CH₂CH₃)₂ | —COO-n-Bu | —C(NH₂)=NH |
| 518 | 1 | —CH(CH₂CH₃)₂ | —COO-i-Bu | —C(NH₂)=NH |
| 519 | 1 | —CH(CH₂CH₃)₂ | —COO-t-Bu | —C(NH₂)=NH |
| 520 | 1 | —CH(CH₂CH₃)₂ | —COO-n-C₅H₁₁ | —C(NH₂)=NH |
| 521 | 1 | —CH(CH₂CH₃)₂ | —SO₂Me | —C(NH₂)=NH |
| 522 | 1 | —CH(CH₂CH₃)₂ | —SO₂Et | —C(NH₂)=NH |
| 523 | 1 | —CH(CH₂CH₃)₂ | —SO₂-i-Pr | —C(NH₂)=NH |
| 524 | 1 | —CH(CH₂CH₃)₂ | —SO₂Ph | —C(NH₂)=NH |
| 525 | 1 | -Benzyl | —H | —C(NH₂)=NH |
| 526 | 1 | -Benzyl | —Me | —C(NH₂)=NH |
| 527 | 1 | -Benzyl | —COCH₃ | —C(NH₂)=NH |
| 528 | 1 | -Benzyl | —COOMe | —C(NH₂)=NH |
| 529 | 1 | -Benzyl | —COOEt | —C(NH₂)=NH |
| 530 | 1 | -Benzyl | —COO-n-Pr | —C(NH₂)=NH |
| 531 | 1 | -Benzyl | —COO-i-Pr | —C(NH₂)=NH |
| 532 | 1 | -Benzyl | —COO-n-Bu | —C(NH₂)=NH |
| 533 | 1 | -Benzyl | —SO₂Me | —C(NH₂)=NH |
| 534 | 1 | 4-F-Benzyl- | —H | —C(NH₂)=NH |
| 535 | 1 | 4-F-Benzyl- | —Me | —C(NH₂)=NH |
| 536 | 1 | 4-F-Benzyl- | —COCH₃ | —C(NH₂)=NH |
| 537 | 1 | 4-F-Benzyl- | —COOEt | —C(NH₂)=NH |
| 538 | 1 | 4-F-Benzyl- | —COO-n-Pr | —C(NH₂)=NH |
| 539 | 1 | 4-F-Benzyl- | —COO-i-Pr | —C(NH₂)=NH |
| 540 | 1 | 4-F-Benzyl- | —COO-n-Bu | —C(NH₂)=NH |
| 541 | 1 | 4-F-Benzyl- | —SO₂Me | —C(NH₂)=NH |
| 542 | 1 | 4-OMe-Benzyl- | —H | —C(NH₂)=NH |
| 543 | 1 | 4-OMe-Benzyl- | —Me | —C(NH₂)=NH |
| 544 | 1 | 4-OMe-Benzyl- | —COCH₃ | —C(NH₂)=NH |
| 545 | 1 | 4-OMe-Benzyl- | —COOEt | —C(NH₂)=NH |
| 546 | 1 | 4-OMe-Benzyl- | —COO-n-Pr | —C(NH₂)=NH |
| 547 | 1 | 4-OMe-Benzyl- | —COO-i-Pr | —C(NH₂)=NH |
| 548 | 1 | 4-OMe-Benzyl- | —COO-n-Bu | —C(NH₂)=NH |
| 549 | 1 | 4-OMe-Benzyl- | —SO₂Me | —C(NH₂)=NH |
| 550 | 1 | —CH₂-cyclo-Hex | —H | —C(NH₂)=NH |
| 551 | 1 | —CH₂-cyclo-Hex | —Me | —C(NH₂)=NH |
| 552 | 1 | —CH₂-cyclo-Hex | —COCH₃ | —C(NH₂)=NH |
| 553 | 1 | —CH₂-cyclo-Hex | —COOEt | —C(NH₂)=NH |
| 554 | 1 | —CH₂-cyclo-Hex | —COO-n-Pr | —C(NH₂)=NH |
| 555 | 1 | —CH₂-cyclo-Hex | —COO-i-Pr | —C(NH₂)=NH |

TABLE 1-continued

| Compound No. | n | R¹ | R² | R³ |
|---|---|---|---|---|
| 556 | 1 | —CH₂-cyclo-Hex | —COO-n-Bu | —C(NH₂)=NH |
| 557 | 1 | —CH₂-cyclo-Hex | —COO-i-Bu | —C(NH₂)=NH |
| 558 | 1 | —CH₂-cyclo-Hex | —SO₂Me | —C(NH₂)=NH |
| 559 | 1 | —CH₂C(CH₃)₃ | —H | —C(NH₂)=NH |
| 560 | 1 | —CH₂C(CH₃)₃ | —Me | —C(NH₂)=NH |
| 561 | 1 | —CH₂C(CH₃)₃ | —COCH₃ | —C(NH₂)=NH |
| 562 | 1 | —CH₂C(CH₃)₃ | —COOEt | —C(NH₂)=NH |
| 563 | 1 | —CH₂C(CH₃)₃ | —COO-n-Pr | —C(NH₂)=NH |
| 564 | 1 | —CH₂C(CH₃)₃ | —COO-i-Pr | —C(NH₂)=NH |
| 565 | 1 | —CH₂C(CH₃)₃ | —COO-n-Bu | —C(NH₂)=NH |
| 566 | 1 | —CH₂C(CH₃)₃ | —COO-i-Bu | —C(NH₂)=NH |
| 567 | 1 | —CH₂C(CH₃)₃ | —SO₂Me | —C(NH₂)=NH |
| 568 | 1 | —(CH₂)₂CH(CH₃)₂ | —H | —C(NH₂)=NH |
| 569 | 1 | —(CH₂)₂CH(CH₃)₂ | —Me | —C(NH₂)=NH |
| 570 | 1 | —(CH₂)₂CH(CH₃)₂ | —COCH₃ | —C(NH₂)=NH |
| 571 | 1 | —(CH₂)₂CH(CH₃)₂ | —COOEt | —C(NH₂)=NH |
| 572 | 1 | —(CH₂)₂CH(CH₃)₂ | —COO-n-Pr | —C(NH₂)=NH |
| 573 | 1 | —(CH₂)₂CH(CH₃)₂ | —COO-i-Pr | —C(NH₂)=NH |
| 574 | 1 | —(CH₂)₂CH(CH₃)₂ | —COO-n-Bu | —C(NH₂)=NH |
| 575 | 1 | —(CH₂)₂CH(CH₃)₂ | —COO-i-Bu | —C(NH₂)=NH |
| 576 | 1 | —(CH₂)₂CH(CH₃)₂ | —SO₂Me | —C(NH₂)=NH |
| 577 | 2 | —Me | —H | —C(NH₂)=NH |
| 578 | 2 | —Me | —Me | —C(NH₂)=NH |
| 579 | 2 | —Me | —COCH₃ | —C(NH₂)=NH |
| 580 | 2 | —Me | —COOEt | —C(NH₂)=NH |
| 581 | 2 | —Me | —COO-n-Pr | —C(NH₂)=NH |
| 582 | 2 | —Me | —COO-i-Pr | —C(NH₂)=NH |
| 583 | 2 | —Me | —COO-n-Bu | —C(NH₂)=NH |
| 584 | 2 | —Me | —COO-i-Bu | —C(NH₂)=NH |
| 585 | 2 | —Me | —SO₂Me | —C(NH₂)=NH |
| 586 | 2 | —Et | —H | —C(NH₂)=NH |
| 587 | 2 | —Et | —Me | —C(NH₂)=NH |
| 588 | 2 | —Et | —COCH₃ | —C(NH₂)=NH |
| 589 | 2 | —Et | —COOEt | —C(NH₂)=NH |
| 590 | 2 | —Et | —COO-n-Pr | —C(NH₂)=NH |
| 591 | 2 | —Et | —COO-i-Pr | —C(NH₂)=NH |
| 592 | 2 | —Et | —COO-n-Bu | —C(NH₂)=NH |
| 593 | 2 | —Et | —COO-i-Bu | —C(NH₂)=NH |
| 594 | 2 | —Et | —SO₂Me | —C(NH₂)=NH |
| 595 | 2 | -n-Pr | —H | —C(NH₂)=NH |
| 596 | 2 | -n-Pr | —Me | —C(NH₂)=NH |
| 597 | 2 | -n-Pr | —COCH₃ | —C(NH₂)=NH |
| 598 | 2 | -n-Pr | —COOEt | —C(NH₂)=NH |
| 599 | 2 | -n-Pr | —COO-n-Pr | —C(NH₂)=NH |
| 600 | 2 | -n-Pr | —COO-i-Pr | —C(NH₂)=NH |
| 601 | 2 | -n-Pr | —COO-n-Bu | —C(NH₂)=NH |
| 602 | 2 | -n-Pr | —COO-i-Bu | —C(NH₂)=NH |
| 603 | 2 | -n-Pr | —SO₂Me | —C(NH₂)=NH |
| 604 | 2 | -i-Pr | —H | —C(NH₂)=NH |
| 605 | 2 | -i-Pr | —Me | —C(NH₂)=NH |
| 606 | 2 | -i-Pr | —COCH₃ | —C(NH₂)=NH |
| 607 | 2 | -i-Pr | —COOEt | —C(NH₂)=NH |
| 608 | 2 | -i-Pr | —COO-n-Pr | —C(NH₂)=NH |
| 609 | 2 | -i-Pr | —COO-i-Pr | —C(NH₂)=NH |
| 610 | 2 | -i-Pr | —COO-n-Bu | —C(NH₂)=NH |
| 611 | 2 | -i-Pr | —COO-i-Bu | —C(NH₂)=NH |
| 612 | 2 | -i-Pr | —SO₂Me | —C(NH₂)=NH |
| 613 | 2 | -n-Bu | —H | —C(NH₂)=NH |
| 614 | 2 | -n-Bu | —Me | —C(NH₂)=NH |
| 615 | 2 | -n-Bu | —COCH₃ | —C(NH₂)=NH |
| 616 | 2 | -n-Bu | —COOEt | —C(NH₂)=NH |
| 617 | 2 | -n-Bu | —COO-n-Pr | —C(NH₂)=NH |
| 618 | 2 | -n-Bu | —COO-i-Pr | —C(NH₂)=NH |
| 619 | 2 | -n-Bu | —COO-n-Bu | —C(NH₂)=NH |
| 620 | 2 | -n-Bu | —COO-i-Bu | —C(NH₂)=NH |
| 621 | 2 | -n-Bu | —SO₂Me | —C(NH₂)=NH |
| 622 | 2 | -i-Bu | —H | —C(NH₂)=NH |
| 623 | 2 | -i-Bu | —Me | —C(NH₂)=NH |
| 624 | 2 | -i-Bu | —COCH₃ | —C(NH₂)=NH |
| 625 | 2 | -i-Bu | —COOEt | —C(NH₂)=NH |
| 626 | 2 | -i-Bu | —COO-n-Pr | —C(NH₂)=NH |
| 627 | 2 | -i-Bu | —COO-i-Pr | —C(NH₂)=NH |
| 628 | 2 | -i-Bu | —COO-n-Bu | —C(NH₂)=NH |
| 629 | 2 | -i-Bu | —COO-i-Bu | —C(NH₂)=NH |
| 630 | 2 | -i-Bu | —SO₂Me | —C(NH₂)=NH |
| 631 | 2 | -cyclobutyl | —H | —C(NH₂)=NH |
| 632 | 2 | -cyclobutyl | —Me | —C(NH₂)=NH |
| 633 | 2 | -cyclobutyl | —COCH₃ | —C(NH₂)=NH |
| 634 | 2 | -cyclobutyl | —COOEt | —C(NH₂)=NH |
| 635 | 2 | -cyclobutyl | —COO-n-Pr | —C(NH₂)=NH |
| 636 | 2 | -cyclobutyl | —COO-i-Pr | —C(NH₂)=NH |
| 637 | 2 | -cyclobutyl | —COO-n-Bu | —C(NH₂)=NH |
| 638 | 2 | -cyclobutyl | —COO-i-Bu | —C(NH₂)=NH |
| 639 | 2 | -cyclobutyl | —SO₂Me | —C(NH₂)=NH |
| 640 | 2 | -cyclopentyl | —H | —C(NH₂)=NH |
| 641 | 2 | -cyclopentyl | —Me | —C(NH₂)=NH |
| 642 | 2 | -cyclopentyl | —COCH₃ | —C(NH₂)=NH |
| 643 | 2 | -cyclopentyl | —COOEt | —C(NH₂)=NH |
| 644 | 2 | -cyclopentyl | —COO-n-Pr | —C(NH₂)=NH |
| 645 | 2 | -cyclopentyl | —COO-i-Pr | —C(NH₂)=NH |
| 646 | 2 | -cyclopentyl | —COO-n-Bu | —C(NH₂)=NH |
| 647 | 2 | -cyclopentyl | —COO-i-Bu | —C(NH₂)=NH |
| 648 | 2 | -cyclopentyl | —SO₂Me | —C(NH₂)=NH |
| 649 | 2 | -Benzyl | —H | —C(NH₂)=NH |
| 650 | 2 | -Benzyl | —Me | —C(NH₂)=NH |
| 651 | 2 | -Benzyl | —COCH₃ | —C(NH₂)=NH |
| 652 | 2 | -Benzyl | —COOEt | —C(NH₂)=NH |
| 653 | 2 | -Benzyl | —COO-n-Pr | —C(NH₂)=NH |
| 654 | 2 | -Benzyl | —COO-i-Pr | —C(NH₂)=NH |
| 655 | 2 | -Benzyl | —COO-n-Bu | —C(NH₂)=NH |
| 656 | 2 | -Benzyl | —COO-i-Bu | —C(NH₂)=NH |
| 657 | 2 | -Benzyl | —SO₂Me | —C(NH₂)=NH |
| 658 | 2 | -i-Pr | —H | —C(NH₂)=NH |
| 659 | 2 | -i-Pr | —Me | —C(NH₂)=NH |
| 660 | 2 | -i-Pr | —COCH₃ | —C(NH₂)=NH |
| 661 | 2 | -i-Pr | —COOEt | —C(NH₂)=NH |
| 662 | 2 | -i-Pr | —COO-n-Pr | —C(NH₂)=NH |
| 663 | 2 | -i-Pr | —COO-i-Pr | —C(NH₂)=NH |
| 664 | 2 | -i-Pr | —COO-n-Bu | —C(NH₂)=NH |
| 665 | 2 | -i-Pr | —COO-i-Bu | —C(NH₂)=NH |
| 666 | 2 | -i-Pr | —SO₂Me | —C(NH₂)=NH |
| 667 | 2 | —CH(CH₂CH₃)₂ | —H | —C(NH₂)=NH |
| 668 | 2 | —CH(CH₂CH₃)₂ | —Me | —C(NH₂)=NH |
| 669 | 2 | —CH(CH₂CH₃)₂ | —COCH₃ | —C(NH₂)=NH |
| 670 | 2 | —CH(CH₂CH₃)₂ | —COOEt | —C(NH₂)=NH |
| 671 | 2 | —CH(CH₂CH₃)₂ | —COO-n-Pr | —C(NH₂)=NH |
| 672 | 2 | —CH(CH₂CH₃)₂ | —COO-i-Pr | —C(NH₂)=NH |
| 673 | 2 | —CH(CH₂CH₃)₂ | —COO-n-Bu | —C(NH₂)=NH |
| 674 | 2 | —CH(CH₂CH₃)₂ | —COO-i-Bu | —C(NH₂)=NH |
| 675 | 2 | —CH(CH₂CH₃)₂ | —SO₂Me | —C(NH₂)=NH |

The methods for the preparation of the compounds of the present invention will be explained below.

Compounds of the present invention can be prepared by combinations of reactions suitable to obtain the respective desired compounds. Typical reaction schemes are exemplified below, however, the methods are not limited to those described below.

Reaction Scheme 1

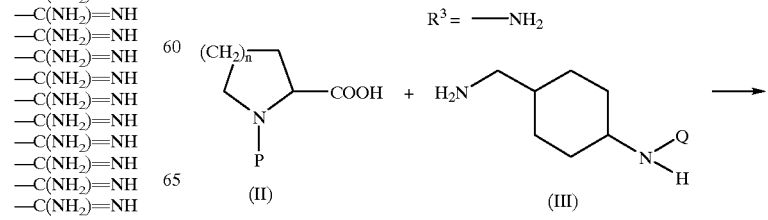

-continued

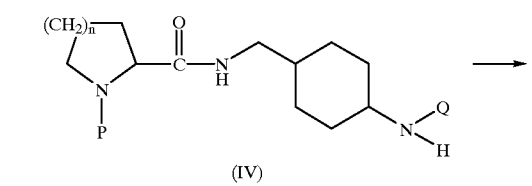

(IV)

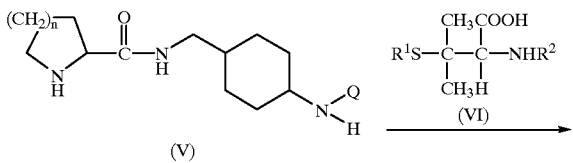

(V)

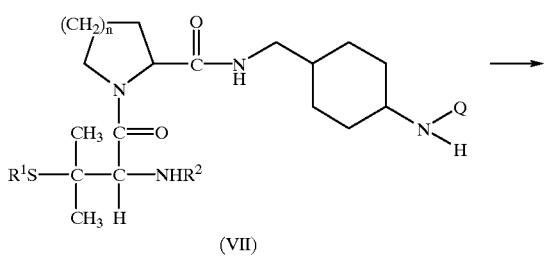

(VII)

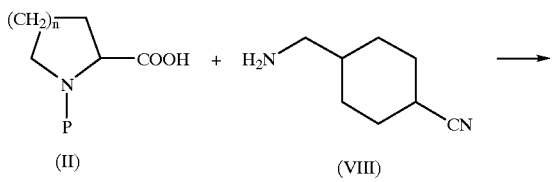

(I)

Reaction Scheme 2

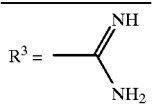

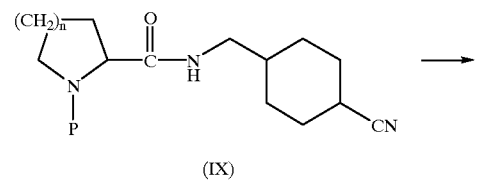

(II)          (VIII)

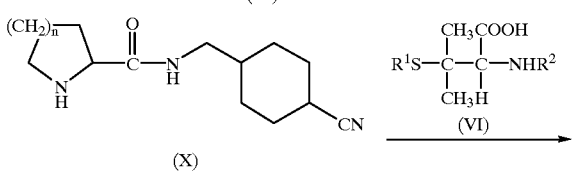

(IX)

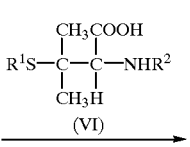

(X)

-continued

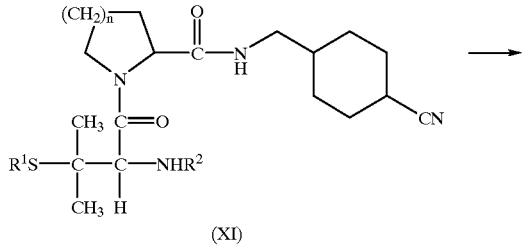

(XI)

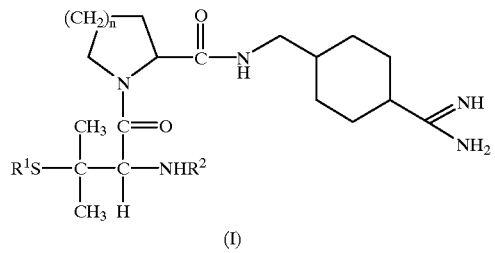

(I)

In the above schemes, $R^1$, $R^2$ and n have the same meanings as those defined above, and P and Q represent a protective group for amino group such as benzyloxycarbonyl group and t-butyloxycarbonyl group.

In the above schemes, a known method for amide synthesis may be used for the preparations of the compounds of formulas (IV), (VII), (IX), and (XI). Examples of applicable methods include, for example, methods using a dehydration-condensing agent such as dicyclohexylcarbodiimide, 1-ethyl-3-(dimethylaminopropyl)carbodiimide, and carbonyldiimidazole, the azide methods, the acid halide methods, the acid anhydride methods, the activated ester methods and the like (see, for example, "Jikken Kagaku Koza," 4th edition, Vol. 22, Organic Syntheses IV, p.259- (1992), Ed. by the Chemical Society of Japan, Maruzen). The reactions may be performed in an inert solvent such as tetrahydrofuran, diethyl ether, and dichloromethane under cooling, at room temperature, or with heating in a conventional manner. In the above reaction schemes, the compounds of formula (V), the compounds of formula (I) in Reaction Scheme 1, and the compounds of formula (X) can be synthesized by carrying out a deprotection reaction according to a method known in the field of peptide chemistry (see, for example, Nobuo, Izumiya et al., "Fundamentals and Experiments of Peptide Syntheses," Maruzen).

The compound of formula (I) in Reaction Scheme 2 may be prepared by subjecting an imidate compound, obtained by treating the compound of formula (XI) with an alcohol and an inorganic acid such as hydrochloric acid, to reaction with ammonia or ammonium salt, or alternatively, by subjecting a thioamide compound, obtained by treating the compound of formula (XI) with hydrogen disulfide in the presence of an organic base such as triethylamine or pyridine, to reaction with a lower alkyl halide compound such as methyl iodide, and then reacting the resulting thioimidate compound with ammonia or ammonium salt.

Each of the compounds obtained as described above can be isolated and purified by conventional chemical techniques such as, for example, extraction, crystallization, recrystallization, or various chromatographic processes.

When the compounds of the present invention are used as medicaments, the compound, per se, may be used. Generally, however, it is preferable that the compound is used in the form of a pharmaceutical composition comprising the compound of the present invention as an active ingredient together with a pharmaceutically acceptable additive. A ratio of the active ingredient to the pharmaceutically acceptable additive may vary in the range of, for example, from 1 to 90% by weight. As pharmaceutical compositions comprising the compound of the present invention, for example, compositions for oral administration such as granules, fine granules, powders, tablets, hard capsules, soft capsules, syrups, emulsions, suspensions, and liquid drugs may be administered, or alternatively, injections can be administered intravenously, intramuscularly, or subcutaneously. The compositions can be used also as suppositories. The compositions can also be provided as powders for injection and used as injections prepared upon use.

As the pharmaceutically acceptable additives, solid or liquid, and organic or inorganic carriers and diluents for pharmaceutical preparations suitable for oral, enteral, or parenteral administration may be used. As excipients used for the preparation of solid pharmaceutical compositions, for example, lactose, saccharose, starch, talc, cellulose, dextrin, china clay, calcium carbonate and the like may be used. Liquid compositions for oral administration such as emulsions, syrups, suspensions, or solutions may contain conventionally-used inert diluents such as water or vegetable oils. These liquid compositions may contain, in addition to the inert diluents, for example, auxiliaries such as moistening agents, suspending aids, sweeteners, aromatics, colorants and preservatives. Liquid compositions thus prepared may be encapsulated into capsules made of an absorbable material such as gelatin. Examples of solvents or suspension mediums used for preparation of the pharmaceutical compositions for parenteral administration such as injections, suppositories and the like include, for example, water, propylene glycol, polyethylene glycol, benzyl alcohol, ethyl oleate, and lecithin. Base materials used for suppositories include, for example, cacao butter, emulsified cacao butter, lauric lipid, and Witepsol. Those pharmaceutical compositions can be manufactured by conventional methods.

Clinical dose for oral administration may generally be 0.01–1000 mg, preferably 10–1000 mg per day for an adult as a weight of the compound of the present invention. However, it is further preferable that the dose may be appropriately increased or decreased depending on age, conditions, and symptoms of a patient. The daily dose of the medicament of the present invention can be administered once a day, or alternatively, two or three times a day with appropriate intervals as divided portions. The dose may be administered intermittently.

When the medicaments are administered as injections, it is desirable that a single dose of 0.001–100 mg for an adult as a weight of the compound of the present invention is administered continuously or intermittently.

EXAMPLES

The present invention will be explained more specifically by referring to the following examples. However, the scope of the present invention is not limited to the following examples.

In the examples below, the following ordinary abbreviations are used: THF: tetrahydrofuran; DMF: N,N-dimethylformamide; DMSO: dimethyl sulfoxide; CDI: carbonyldiimidazole; DPPA: diphenylphosphoryl azide; Z: benzyloxycarbonyl; and Boc: tertiary-butyloxycarbonyl.

In the physicochemical data, NMR represents nuclear magnetic resonance spectrum, wherein values are shown as δ (delta) values in ppm which are ordinarily used for indicating chemical shifts. TMS (tetramethylsilane) was used as an internal standard. Parenthesized numbers following δ values indicate the numbers of hydrogen atoms, and as to symbols after the parenthesized number, "s" represents singlet; "d" represents doublet; "t" represents triplet; "q" represents quartet; "m" represents multiplet, and "br" represents a broad absorption peak.

IR represents infrared absorption spectrum, and the spectrum was measured as a potassium bromide tablet unless otherwise specified. Numerical values are indicated as wave numbers in $cm^{-1}$. Only major absorption peaks are indicated. The symbol "mp" means melting point, and uncorrected values as 0° C. are indicated.

Example 1

Synthesis of trans-4-amino-[(S)-N-[(S)-2-propoxycarbonylamino-3-isopropylthio-3-methylbutanoyl]prolyl]aminomethylcyclohexane (Compound No. 51 in Table 1) hydrochloride a) Trans-4-t-butoxycarbonylamino-benzyloxycarbonylaminomethylcyclohexane To a solution of trans-4-aminomethylcyclohexanecarboxylic acid (15.7 g, 100 mmol) and sodium hydroxide (4.0 g, 100 mmol) in water (30 ml), benzyloxycarbonyl chloride (15.6 ml, 110 mmol) and a solution of sodium hydroxide (4.4 g, 110 mmol) in water (30 ml) were simultaneously and slowly added dropwise at 0° C. After stirring was continued for four hours, the mixture was extracted once with ether, and 1N hydrochloric acid was added to the aqueous layer to adjust its pH to 2. The deposited white solid was collected by filtration and dried.

Triethylamine (8.3 ml, 60 mmol) and DPPA (13.7 g, 50 mmol) were added to a solution of the above-obtained compound (12.8 g, 50 mmol) in t-butanol (150 ml), and the mixture was heated under reflux for eight hours. After the solvent was evaporated, the residue was added with water, and then the mixture was extracted with chloroform. The organic layer was washed once with 5% aqueous sodium carbonate, once with 5% aqueous acid potassium sulfate, twice with water, and then once with saturated brine. After the layer was dried over sodium sulfate, the solvent was evaporated. The residue was purified by silica gel column chromatography (hexane/ethyl acetate) to obtain the title compound a) (8.6 g, yield; 47%).

NMR (CDCl$_3$): 0.85–1.37 (m, 14H), 1.60–1.85 (m, 4H), 2.84 (t, 1H), 3.12 (br, 1H), 5.00 (s, 2H), 6.62 (d, 1H), 7.23–7.39 (m, 6H).

b) Trans-4-t-butoxycarbonylamino-[(S)-N-benzyloxycarbonylprolyl]aminomethylcyclohexane The compound obtained in a) (4.4 g, 12 mmol) was dissolved in methanol (200 ml), and the solution was subjected to catalytic reduction in the presence of palladium black (0.4 g) at ambient temperature under atmospheric pressure. After the completion of the reaction, the catalyst was removed by filtration, and the solvent was evaporated.

CDI (2.0 g, 12 mmol) was added to a solution of (S)-Z-proline (3.0 g, 12 mmol) in THF (30 ml) at 0° C. After stirring was continued for three hours, the mixture was added with a solution of the above-obtained compound in THF (150 ml) at 0° C. After stirring for six hours, the solvent was evaporated, and the residue was added with water (50 ml). The mixture was extracted with chloroform, and the organic layer was washed three times with water and once with saturated brine. After the layer was dried with sodium sulfate, the solvent was evaporated. The residue was purified by silica gel chromatography (chloroform/methanol) to obtain the title compound b) (4.2 g, yield; 77%).

NMR (CDCl$_3$): 0.85–1.06 (m, 4H), 1.44 (s, 9H), 1.60–2.35 (m, 9H), 2.94–3.20 (m, 2H), 3.20–3.55 (m, 3H), 4.31 (br, 1H), 4.47 (br, 1H), 5.14 (s, 2H), 6.90 (br, 1H), 7.15–7.40 (m, 5H)

c) Trans-4-t-butoxycarbonylamino-[(S)-N-[(S)-2-propoxycarbonylamino-3-isopropylthio- 3-methylbutanoyl]prolyl]aminomethylcyclohexane The compound obtained in b) (3.6 g 7.9 mmol) was dissolved in methanol (50 ml), and the solution was subjected to catalytic reduction in the presence of palladium black (0.3 g) at ambient temperature under atmospheric pressure. After the completion of the reaction, the catalyst was removed by filtration, and then the solvent was evaporated.

The oily product obtained above, (S)-2-propoxycarbonylamino-3-isopropylthio-3-methylbutanoic acid (2.4 g, 8.7 mmol), and triethylamine (1.58 g, 15.6 mmol) were dissolved in dichloromethane (55 ml), and the solution was added dropwise with a solution of diethyl phosphorocyanidate (DEPC, 1.4 g, 8.7 mmol) in dichloromethane (10 ml) at 0° C. After the temperature was raised up to room temperature, the mixture was stirred for an additional 24 hours and then added with water. The mixture was extracted twice with dichloromethane, and the organic layer was dried over sodium sulfate.

After the solvent was evaporated, the resulting residue was purified by silica gel column chromatography (chloroform/methanol) to obtain the title compound c) (3.9g, yield; 85%).

NMR (CDCl$_3$): 7.18 (t, 1H), 5.59 (d, 1H), 4.61 (d, 1H), 4.34 (d, 2H), 4.20–3.85 (m, 3H), 3.72 (m, 1H), 3.33 (m, 1H), 3.90–3.20 (m, 3H), 2.37 (m, 1H), 2.10–0.90 (m, 14H), 1.47 (s, 3H), 1.43 (s, 9H), 1.40 (s, 3H), 1.29 (dd, 6H), 0.94 (t, 3H).

d) Trans-4-amino-[(S)-N-[(S)-2-propoxycarbonylamino-3-isopropylthio-3-methylbutanoyl]prolyl]aminomethylcyclohexane hydrochloride A solution of the compound obtained in c) (3.9 g, 6.7 mmol) in chloroform (5 ml) was added dropwise with a 4N solution of hydrochloric acid in ethyl acetate (37 ml) at 0° C. After the mixture was stirred for one hour, the solvent was evaporated. The resulting residue was suspended and washed in ether, and then collected by filtration to obtain the title compound d) (3.1 g, yield; 90%).

NMR (CDCl$_3$): 8.34 (br, 3H), 7.21 (t, 1H), 5.61 (d, 1H), 4.59 (d, 1H), 4.31 (d, 1H), 4.07–3.92 (m, 3H), 3.74 (m, 1H), 3.20–2.90 (m, 2H), 2.36 (m, 1H), 2.20–1.40 (m, 12H), 1.47 (s, 3H), 1.29 (dd, 6H), 0.95 (t, 3H), 1.10–0.90 (m, 2H); IR: 3344, 2974, 2876, 1689, 1637, 1527, 1448, 1313, 1240, 1060.

In similar manners to those described above, the compounds of Examples 2–39 set out below were obtained.

Example 2

Trans-4-amino-[(S)-N-[(S)-2-ethoxycarbonylamino-3-isopropylthio-3-methylbutanoyl]prolyl]aminomethylcyclohexane (Compound No. 50 in Table 1) hydrochloride NMR (CDCl$_3$): 8.32 (br, 3H), 7.22 (t, 1H), 5.60 (d, 1H), 4.59 (m, 1H), 4.30 (d, 1H), 4.20–3.90 (m, 3H), 3.71 (m, 1H), 3.20–2.89 (m, 4H), 2.36 (m, 1H), 2.16 (m, 2H), 2.05 (m, 3H), 1.90–1.20 (m, 5H), 1.47 (s, 3H), 1.40 (s, 3H), 1.34–1.21 (m, 9H), 1.05–0.91 (m, 2H); IR: 3352, 2934, 2872, 1693, 1637, 1535, 1444, 1367, 1302, 1242.

Example 3

Trans-4-amino-[(S)-N-[(S)-2-ethoxycarbonylamino-3-isobutylthio-3-methylbutanoyl]proly]aminomethylcyclohexane (Compound No. 97 in Table 1) hydrochloride NMR (CDCl$_3$): 8.32 (br, 3H), 7.19 (t, 1H), 5.58 (d, 1H), 4.57 (d, 1H), 4.30 (d, 2H), 3.93 (m, 1H), 3.76 (m, 1H), 3.20–2.90 (m, 3H), 2.47–2.30 (m, 3H), 2.25–2.15 (m, 2H), 2.10–1.40 (m, 9H), 1.48 (s, 3H), 1.38 (s, 3H), 1.27 (t, 3H), 0.98 (dd, 6H), 1.05–0.90 (m, 2H); IR: 3354, 2957, 2868, 1691, 1639, 1535, 1444, 1386, 1242, 1055.

Example 4

Trans-4-amino-[(S)-N-[(S)-2-isopropoxycarbonylamino-3-isopropylthio-3-methylbutanoyl]prolyl]aminomethylcyclohexane (Compound No. 52 in Table 1) hydrochloride NMR (CDCl$_3$): 8.33 (br, 3H), 7.24 (t, 1H), 5.53 (d, 1H), 4.82 (m, 1H), 4.59 (m, 1H), 4.28 (d, 1H), 3.97 (m, 1H), 3.71 (m, 1H), 3.12–2.85 (m, 4H), 2.35 (m, 1H), 2.20 (m, 2H), 2.15–1.40 (m, 8H), 1.48 (s, 3H), 1.40 (s, 3H), 1.29 (dd, 6H), 1.26 (d, 6H), 1.10–0.90 (m, 2H); IR: 3344, 2935, 2866, 1685, 1637, 1523, 1446, 1242, 1111, 1043.

Example 5

Trans-4-amino-[(S)-N-[(S)-2-methoxycarbonylamino-3-ethylthio-3-methyl-butanoyl]prolyl]aminomethylcyclohexane (Compound No. 12 in Table 1) hydrochloride NMR (CDCl$_3$): 8.31 (br, 3H), 7.19 (t, 1H), 5.68 (d, 1H), 4.57 (d, 1H), 4.35 (d, 1) 3.91 (m, 1H), 3.74 (m, 1H), 3.69 (s, 3H), 3.22–2.94 (m, 3H), 2.70 –2.45(m, 3H), 2.40–1.40 (m, 10H), 1.44 (s, 3H), 1.39 (s, 3H), 1.21 (t, 3H), 1.10 –0.90 (m, 2H); IR: 3383, 2935, 2872, 1701, 1637, 1541, 1448, 1298, 1244, 1057.

Example 6

Trans-4-amino-[(S)-N-[(S)-2-methoxycarbonylamino-3-isopropylthio-3-methylbutanoyl]proly]aminomethylcyclohexane (Compound No. 49 in Table 1) hydrochloride.

NMR (CDCl$_3$): 8.32 (br, 3H), 7.18 (t, 1H), 5.67 (d, 1H), 4.58 (d, 1H), 4.33 (d, 1H), 3.94 (m, 1H), 3.70 (m, 1H), 3.69 (s, 1H), 3.20–2.94 (m, 4H), 2.37 (m, 1H), 2.20–1.40 (m, 10H), 1.47 (s, 3H), 1.40 (s, 3H), 1.29 (dd, 6H), 1.10–0.90 (m, 2H); IR: 3356, 2934, 2868, 1701, 1643, 1535, 1446, 1300, 1242, 1053.

Example 7

Trans-4-amino-[(S)-N-[(S)-2-methoxycarbonylamino-3-cyclopentylthio-3-methylbutanoyl]prolyl]aminomethylcyclohexane (Compound No. 163 in Table 1) hydrochloride NMR (CDCl$_3$): 8.33 (br, 3H), 7.21 (t, 1H), 5.64 (d, 1H), 4.59 (d, 1H), 4.34 (d, 1H), 3.94 (m, 1H), 3.72 (m, 1H), 3.69 (s, 3H), 3.20–2.90 (m, 4H), 2.38 (m, 1H), 2.20–1.20 (m, 18H), 1.47 (s, 3H), 1.39 (s, 3H), 1.10–0.90 (m, 2H); IR: 3362, 2955, 2868, 1701, 1639, 1535, 1446, 1298, 1242, 1055.

Example 8

Trans-4-amino-[(S)-N-[(S)-2-methylsulfonylamino-3-ethylthio-3-methyl-butanoyl]prolyl]aminomethylcyclohexane (Compound No. 23 in Table 1) hydrochloride NMR (CDCl$_3$): 8.13 (br, 3H), 6.99 (t, 1H), 5.97 (d, 1H), 4.52 (d, 1H), 4.25 (t, 1H), 4.15 (d, 1H), 4.03–3.81 (m, 2H), 3.20–2.90 (m, 3H), 3.08 (s, 3H), 2.70–2.50 (m, 2H), 2.50–1.40 (m, 10H), 1.42 (s, 3H), 1.39 (s, 3H), 1.29–1.16 (m, 3H), 1.10–0.90 (m, 2H); IR: 3383, 2934, 2866, 1637, 1543, 1450, 1317, 1151, 1035, 983.

Example 9

Trans-4-amino-[(S)-N-[(S)-2-amino-3-ethylthio-3-methylbutanoyl]prolyl]-aminomethylcyclohexane (Compound No. 8 in Table 1) dihydrochloride NMR (CDCl$_3$): 8.72 (br, 3H), 8.31 (t, 1H), 8.18 (br, 3H), 4.44 (m, 1H), 4.27 (m, 1H), 4.06 (d, 1H), 3.83–3.60 (m, 4H), 3.13 (m, 1H), 3.04–2.87 (m, 2H), 2.61–2.52 (m, 2H), 2.24–1.40 (m, 8H), 1.47 (s, 3H), 1.42 (s, 3H), 1.29–1.22 (m, 3H), 1.10–0.90 (m, 2H); IR: 3476, 3285, 3084, 2941, 1647, 1493, 1446, 1346, 1116, 1049.

Example 10

Trans-4-amino-[(S)-N-[(S)-2-methoxycarbonylamino-3-propylthio-3-methylbutanoyl]prolyl]aminomethylcyclohexane (Compound No. 30 in Table 1) hydrochloride NMR (CDCl$_3$): 8.31 (br, 3H), 7.16 (t, 1H), 5.64 (d, 1H), 4.58 (d, 1H), 4.34 (d, 1H), 3.91 (m, 1H), 3.76 (m, 1H), 3.69 (s, 3H), 3.20–2.90 (m, 3H), 2.60–2.34 (m, 3H), 2.14 (m, 2H), 2.10–1.40 (m, 10H), 1.43 (s, 3H), 1.39 (s, 3H), 0.99 (t, 3H), 1.10–0.90 (m, 2H); IR: 3358, 2935, 2866, 1703, 1643, 1533, 1446, 1298, 1240, 1055.

Example 11

Trans-4-amino-[(S)-N-[(S)-2-methoxycarbonylamino-3-isobutylthio-3-methylbutanoyl]prolyl]aminomethylcyclohexane (Compound No. 96 in Table 1) hydrochloride NMR (CDCl$_3$): 8.33 (br, 3H), 7.16 (t, 1H), 5.64 (d, 1H), 4.57 (d, 1H), 4.33 (d, 1H), 3.91 (m, 1H), 3.75 (m, 1H), 3.69 (s, 3H), 3.20–2.90 (m, 3H), 2.50–2.30 (m, 3H), 2.15 (m, 2H), 2.10–1.40 (m, 9H), 1.42 (s, 3H), 1.38 (s, 3H), 0.98 (dd, 6H), 1.10–0.90 (m, 2H); IR: 3429, 2957, 2868, 1701, 1639, 1541, 1448, 1321, 1244, 1055.

Example 12

Trans-4-amino-[(S)-N-[(S)-2-ethoxycarbonylamino-3-ethylthio-3-methyl-butanoyl]prolyl]aminomethylcyclohexane (Compound No. 13 in Table 1) hydrochloride NMR (CDCl$_3$): 8.33 (br, 3H), 7.17 (t, 1H), 5.57 (d, 1H), 4.57 (d, 1H), 4.33 (d, 1H), 4.22–4.05 (m, 2H), 3.91 (m, 1H), 3.82 (m, 1H), 3.20–2.90 (m, 3H), 2.70–2.50 (m, 2H), 2.36 (m, 1H), 2.22–1.40 (m, 10H), 1.44 (s, 3H), 1.39 (s, 3H), 1.27 (t, 3H), 1.22 (t, 3H), 1.20–0.90 (m, 2H); IR: 3354, 2934, 2872, 1701, 1637, 1523, 1444, 1298, 1242, 1057.

Example 13

Trans-4-amino-[(S)-N-[(S)-2-ethoxycarbonylamino-3-propylthio-3-methyl-butanoyl]prolyl]aminomethylcyclohexane (Compound No. 31 in Table 1) hydrochloride NMR (CDCl$_3$): 8.33 (br, 3H), 7.18 (t, 1H), 5.57 (d, 1H), 4.58 (d, 1H), 4.32 (d, 1H), 4.22–4.05 (m, 2H), 3.96 (m, 1H), 3.76 (m, 1H), 3.20–2.90 (m, 3H), 2.60–2.47 (m, 2H), 2.36 (m, 1H), 2.25–1.40 (m, 12H), 1.49 (s, 3H), 1.43 (s, 3H), 1.30 (t, 3H), 1.00 (t, 3H), 1.16–0.91 (m, 2H); IR: 3441, 2939, 1641, 1533, 1442, 1300, 1242, 1192, 1170, 1055.

Example 14

Trans-4-amino-[(S)-N-[(S)-2-ethoxycarbonylamino-3-cyclopentylthio-3-methylbutanoyl]prolyl] aminomethylcyclohexane (Compound No. 164 in Table 1) hydrochloride NMR (CDCl$_3$): 8.32 (br, 3H), 7.23 (t, 1H), 5.60 (d, 1H), 4.59 (d, 1H), 4.31 (d, 1H), 4.17–4.02 (m, 2H), 3.95 (m, 1H), 3.71 (m, 1H), 3.22–2.94 (m, 4H), 2.36 (m, 1H), 2.36 (m, 1H), 2.26–1.40 (m, 18H), 1.47 (s, 3H), 1.39 (s, 3H), 1.27 (t, 3H), 1.10–0.90 (m, 2H); IR: 3346, 2939, 2868, 1695, 1641, 1533, 1444, 1300, 1240, 1055.

Example 15

Trans-4-amino-[(S)-N-[(S)-2-ethoxycarbonylamino-3-phenylmethylthio-3-methylbutanoyl]prolyl] aminomethylcyclohexane (Compound No. 214 in Table 1) hydrochloride NMR (CDCl$_3$): 8.32 (br, 3H), 7.35–7.24 (m, 5H), 7.16 (t, 1H), 5.57 (d, 1H), 4.56 (d, 1H), 4.22 (d, 1H), 4.20–4.05 (m, 2H), 3.85 (m, 1H), 3.78 (d, 2H), 3.85 (m, 1H), 3.62 (m, 1H), 3.20–2.90 (m, 3H), 2.32 (m, 1H), 2.25–1.40 (m, 10H), 1.46 (s, 3H), 1.40 (s, 3H), 1.30 (t, 3H), 1.20–0.90 (m, 2H) IR: 3348, 2935, 2874, 1697, 1637, 1541, 1448, 1298, 1242, 1055.

Example 16

Trans-4-amino-[(S)-N-[(S)-2-propoxycarbonylamino-3-propylthio-3-methylbutanoyl]prolyl]aminomethylcyclohexane (Compound No. 32 in Table 1) hydrochloride NMR (CDCl$_3$): 8.33 (br, 3H), 7.19 (t, 1H), 5.57 (d, 1H), 4.57 (d, 1H), 4.31 (d, 1H), 4.11–3.87 (m, 3H), 3.74 (m, 1H), 3.20–2.90 (m, 3H), 2.60–2.40 (m, 2H), 2.34 (m, 1H), 2.15 (m, 2H), 2.10–1.40 (m, 12H), 1.43 (s, 3H), 1.39 (s, 3H), 0.99 (t, 3H), 0.95 (t, 3H), 1.10–0.90 (m, 2H); IR: 3344, 2964, 2878, 1695, 1639, 1529, 1442, 1296, 1240, 1060.

Example 17

Trans-4-amino-[(S)-N-[(S)-2-propoxycarbonylamino-3-cyclopentylthio-3-methylbutanoyl]prolyl]aminomethylcyclohexane (Compound No. 165 in Table 1) hydrochloride NMR (CDCl$_3$): 8.32 (br, 3H), 7.21 (t, 1H), 5.59 (d, 1H), 4.58 (d, 1H), 4.32 (d, 1H), 4.13–3.93 (m, 3H), 3.74 (m, 1H), 3.21–2.90 (m, 4H), 2.34 (m, 1H), 2.25–1.40 (m, 20H), 1.47 (s, 3H), 1.39 (s, 3H), 0.95 (t, 3H), 1.10–0.90 (m, 2H); IR: 3348, 2959, 2870, 1693, 1641, 1529, 1446, 1294, 1240, 1060.

Example 18

Trans-4-amino-[(S)-N-[(S)-2-propoxycarbonylamino-3-isobutylthio-3-methylbutanoyl]prolyl]aminomethylcyclohexane (Compound No. 98 in Table 1) hydrochloride NMR (CDCl$_3$): 8.30 (br, 3H), 7.25 (t, 1H), 5.61 (d, 1H), 4.57 (d, 1H), 4.29 (d, 1H), 3.90 (m, 3H), 3.74 (m, 1H), 3.20–2.90 (m, 1H), 2.40 (m, 2H), 2.30 (m, 1H), 2.16 (m, 2H), 2.10–1.40 (m, 11H), 1.42 (s, 3H), 1.39 (s, 3H), 0.98 (d, 6H), 0.94 (t, 3H), 1.10–0.90 (m, 2H); IR: 3356, 2934, 2883, 1693, 1637, 1527, 1448, 1298, 1240, 1060.

Example 19

Trans-4-amino-[(S)-N-[(S)-2-propoxycarbonylamino-3-butylthio-3-methyl-butanoyl]prolyl]aminomethylcyclohexane (Compound No. 79 in Table 1) hydrochloride NMR (CDCl$_3$): 8.32 (br, 3H), 7.19 (t, 1H), 5.58 (d, 1H), 4.56 (d, 1H), 4.32 (d, 1H), 3.90 (m, 3H), 3.74 (m, 1H), 3.20–2.90 (m, 3H), 2.65–2.46 (m, 2H), 2.34 (m, 1H), 2.16 (m, 2H), 2.10–1.40 (m, 14H), 1.43 (s, 3H), 1.39 (s, 3H), 0.95 (t, 3H), 0.92 (t, 3H), 1.10–0.90 (m, 2H); IR: 3344, 2934, 2874, 1695, 1641, 1529, 1439, 1296, 1240, 1060.

Example 20

Trans-4-amino-[(S)-N-[(S)-2-propoxycarbonylamino-3-cyclohexylmethyl-thio-3-methylbutanoyl]prolyl]aminomethylcyclohexane (Compound No. 241 in Table 1) hydrochloride NMR (CDCl$_3$): 8.31 (br, 3H), 7.20 (t, 1H), 5.59 (d, 1H), 4.58 (d, 1H), 4.30 (d, 1H), 4.15–3.90 (m, 3H), 3.77 (m, 1H), 3.20–2.90 (m, 3H), 2.47–2.30 (m, 3H), (m, 3H), 2.18 (m, 2H), 2.10–1.20 (m, 19H), 1.42 (s, 3H), 1.38 (s, 3H), 0.95 (t, 3H), 1.10–0.90 (m, 2H); IR: 3350, 2926, 2852, 1697, 1639, 1533, 1448, 1302, 1240, 1060.

Example 21

Trans-4-amino-[(S)-N-[(S)-2-propoxycarbonylamino-3-cyclobutylthio-3-methylbutanoyl]prolyl]aminomethylcyclohexane (Compound No. 126 in Table 1) hydrochloride NMR (CDCl$_3$): 8.30 (br, 3H), 7.19 (t, 1H), 5.58 (d, 1H), 4.57 (d, 1H), 4.29 (d, 1H), 4.14–3.90 (m, 3H), 3.75 (m, 1H), 3.22–2.92 (m, 3H), 2.51–2.32 (m, 3H), 2.25–1.20 (m, 17H), 1.42 (s, 3H), 1.38 (s, 3H), 0.95 (t, 3H), 1.10–0.90 (m, 2H); IR: 3358, 2972, 2874, 1697, 1639, 1535, 1440, 1294, 1240, 1060.

Example 22

Trans-4-amino-[(S)-N-[(S)-2-propoxycarbonylamino-3-(1-ethylpropyl)-thio-3-methylbutanoyl]prolyl]aminomethylcyclohexane (Compound No. 182 in Table 1) hydrochloride NMR (CDCl$_3$): 8.31 (br, 3H), 7.27 (t, 1H), 5.65 (d, 1H), 4.60 (d, 1H), 4.24 (d, 1H), 4.16–3.88 (m, 3H), 3.67 (m, 1H), 3.22–3.00 (m, 2H), 2.95 (m, 1H), 2.54 (m, 1H), 2.35 (m, 1H), 2.17 (m, 2H), 2.10–1.40 (m, 17H), 1.44 (s, 3H), 1.41 (s, 3H), 0.98 (t, 3H), 1.10–0.90 (m, 2H); IR: 3425, 2966, 2878, 1701, 1641, 1537, 1446, 1292, 1240, 1060.

Example 23

Trans-4-amino-[(S)-N-[(S)-2-isopropoxycarbonylamino-3-phenylmethyl-thio-3-methylbutanoyl]prolyl]aminomethylcyclohexane (Compound No. 216 in Table 1) hydrochloride NMR (CDCl$_3$): 8.33 (br, 3H), 7.32 (m, 5H), 7.21 (br, 1H), 5.52 (br, 1H), 4.80 (m, 1H), 4.58 (d, 1H), 4.21 (d, 1H), 3.80 (m, 3H), 3.61 (m, 1H), 3.22–2.90 (m, 3H), 2.40–2.18 (m, 3H), 2.10–1.76 (m, 4H), 1.47 (s, 3H), 1.41 (s, 3H), 1.62–1.39 (m, 4H), 1.26 (m, 6H), 0.99 (m, 2H); IR: 3349, 2978, 2935, 1692, 1644, 1497, 1453, 1242, 1111.

Example 24

Trans-4-amino-[(S)-N-[(S)-2-isopropoxycarbonylamino-3-propylthio-3-methylbutanoyl]prolyl]aminomethylcyclohexane (Compound No. 33 in Table 1) hydrochloride NMR (CDCl$_3$): 8.32 (br, 3H), 7.20 (br, 1H), 5.50 (d, 1H), 4.83 (m, 1H), 4.57 (d, 1H), 4.32 (d, 1H), 3.92 (m, 1H), 3.77 (m, 1H), 3.11 (m, 2H), 2.98 (m, 1H), (m, 1H), 2.50 (m, 2H), 2.37 (m, 1H), 2.20 (m, 2H), 2.07–1.78 (m, 5H), 1.56 (m, 5H), 1.43 (s, 3H), 1.39 (s, 3H), 1.26 (d, 3H), 1.24 (d, 3H), 0.99 (t, 3H), 0.98 (m, 2H); IR: 3345, 2936, 1688, 1640, 1534, 1447, 1242, 1111.

Example 25

Trans-4-amino-[(S)-N-[(S)-2-isopropoxycarbonylamino-3-butylthio-3-methylbutanoyl]prolyl]aminomethylcyclohexane (Compound No. 80 in Table 1) hydrochloride NMR (CDCl$_3$): 8.31 (br, 3H), 7.21 (br, 1H), 5.51 (d, 1H), 4.83 (m, 1H), 4.57 (d, 1H), 4.32 (d, 1H), 3.93 (m, 1H), 3.77 (m, 1H), 3.20–2.90 (m, 3H), 2.53 (m, 2H), 2.38 (m, 1H), 2.17 (m, 2H), 1.99 (m, 5H), 1.83 (m, 2H), 1.51 (m, 5H), 1.43 (s, 3H), 1.38 (s, 3H), 1.26 (d, 3H), 1.24 (d, 3H), 1.04–0.90 (m, 2H), 0.92 (t, 3H); IR: 3346, 2934, 2872, 1686, 1638, 1541, 1439, 1242, 1111.

Example 26

Trans-4-amino-[(S)-N-[(S)-2-isopropoxycarbonylamino-3-isobutylthio-3-methylbutanoyl]prolyl]aminomethylcyclohexane (Compound No. 99 in Table 1) hydrochloride NMR (CDCl$_3$): 8.32 (br, 3H), 7.23 (br, 1H), 5.51 (d, 1H), 4.82 (m, 1H), 4.58 (d, 1H), 4.29 (d, 1H), 3.95 (m, 1H), 3.75 (m, 1H), 3.12 (m, 1H), 2.96 (m, 1H), 2.42 (m, 1H), 2.35 (m, 2H), 2.18 (m, 2H), 1.99 (m, 2H), 1.81 (m, 5H), 1.51 (m, 2H), 1.42 (s, 3H), 1.38 (s, 3H), 1.26 (d, 3H), 1.24 (d, 3H), 1.00 (d, 3H), 0.98 (d, 3H), 0.98 (m, 2H); IR: 3345, 2957, 1688, 1640, 1626, 1449, 1242, 1111.

Example 27

Trans-4-amino-[(S)-N-[(S)-2-isopropoxycarbonylamino-3-cyclopentylthio-3-methylbutanoyl]prolyl]aminomethylcyclohexane (Compound No. 172 in Table 1) hydrochloride NMR (CDCl$_3$): 8.31 (br, 3H), 7.23 (br, 1H), 5.53 (d, 1H), 4.83 (m, 1H), 4.59 (d, 1H), 4.32 (d, 1H), 3.94 (m, 1H), 3.74 (m, 1H), 3.09 (m, 3H), 2.94 (m, 1H), 2.39 (m, 1H), 2.19 (m, 2H), 1.99 (m, 5H), 1.83 (m, 2H), 1.71 (m, 2H), 1.54 (m, 7H), 1.46 (s, 3H), 1.46 (s, 3H), 1.39 (s, 3H), 1.26 (d, 3H), 1.24 (d, 3H), 1.00 (m, 2H); IR: 3349, 2942, 2868, 1692, 1640, 1530, 1447, 1240, 1111.

Example 28

Trans-4-amino-[(S)-N-[(S)-2-isobutyloxycarbonylamino-3-cyclopentylthio-3-methylbutanoyl]prolyl]aminomethylcyclohexane (Compound No. 167 in Table 1) hydrochloride NMR (CDCl$_3$): 8.31 (br, 3H), 7.21 (t, 1H), 5.62 (d, 1H), 4.57 (d, 1H), 4.33 (d, 1H), 4.00–3.85 (m, 2H), 3.85–3.70 (m, 2H), 3.20–2.85 (m, 4H), 2.40–1.40 (m, 20H), 1.47 (s, 3H), 1.43 (s, 3H), 1.10–0.90 (m, 2H), 0.94 (d, 6H); IR: 3356, 2966, 2874, 1701, 1637, 1541, 1458, 1296, 1240, 1059.

Example 29

Trans-4-amino-[(S)-N-[(S)-2-isobutyloxycarbonylamino-3-isopropylthio-3-methylbutanoyl]prolyl]aminomethylcyclohexane (Compound No. 54 in Table 1) hydrochloride NMR (CDCl$_3$): 8.31 (br, 3H), 7.21 (t, 1H), 5.63 (d, 1H), 4.58 (d, 1H), 4.31(d, 1H), 4.05–3.85 (m, 2H), 3.80–3.70 (m, 2H), 3.20–2.90 (m, 4H), 2.34 (m, 1H), 2.20–1.40 (m, 11H), 1.47 (s, 3H), 1.40 (s, 3H), 1.30 (dd, 6H), 0.93 (d, 6H), 1.10–0.90 (m, 2H) IR: 3346, 2935, 2876, 1699, 1637, 1527, 1448, 1292, 1240, 1053.

Example 30

Trans-4-amino-[(S)-N-[(S)-2-propoxycarbonylamino-3-(3'-methylbutyl-thio)-3-methylbutanoyl]prolyl]aminomethylcyclohexane (Compound No. 255 in Table 1) hydrochloride NMR (CDCl$_3$): 8.32 (br, 3H), 7.19 (t, 1H), 5.59 (d, 1H), 4.58 (d, 1H), 4.32 (d, 1H), 4.15–3.90 (m, 3H), 3.80 (m, 1H), 3.20–2.90 (m, 3H), 2.65–2.45 (m, 2H), 2.35 (m, 1H), 2.30–1.40 (m, 15H), 1.43 (s, 3H), 1.38 (s, 3H), 0.95 (t, 3H), 0.90 (d, 6H), 1.10–0.90 (m, 2H); IR: 3354, 2934, 2874, 1701, 1637, 1541, 1439, 1298, 1240, 1060.

Example 31

Trans-4-amino-[(S)-N-[(S)-2-isobutyloxycarbonylamino-3-propylthio-3-methylbutanoyl]prolyl]aminomethylcyclohexane (Compound No. 35 in Table 1) hydrochloride NMR (CDCl$_3$): 8.32 (br, 3H), 7.19 (t, 1H), 5.60 (d, 1H), 4.57 (d, 1H), 4.33 (d, 1H), 3.89 (dd, 2H), 3.77 (m, 2H), 3.20–2.90 (m, 3H), 2.62–2.45 (m, 2H), 2.34 (m, 1H), 2.18 (m, 2H), 2.10–1.40 (m, 11H), 1.43 (s, 3H), 1.39 (s, 3H), 0.99 (t, 3H), 0.93 (d, 6H), 1.10–0.90 (m, 2H); IR: 3346, 2962, 2878, 1693, 1637, 1527, 1448, 1294, 1240, 1053.

Example 32

Trans-4-amino-[(S)-N-[(S)-2-isobutyloxycarbonylamino-3-isobutylthio-3-methylbutanoyl]prolyl]aminomethylcyclohexane (Compound No. 101 in Table 1) hydrochloride NMR (CDCl$_3$): 8.31 (br, 3H), 7.19 (t, 1H), 5.60 (d, 1H), 4.58 (d, 1H), 4.31 (d, 1H), 4.00–3.85 (m, 2H), 3.75 (m, 2H), 3.20–2.90 (m, 3H), 2.18 (m, 2H), 2.10–1.40 (m, 10H), 1.42 (s, 3H), 1.39 (s, 3H), 0.98 (dd, 6H), 0.94(d, 6H), 1.10–0.90 (m, 2H); IR: 3346, 2959, 2870, 1701, 1637, 1533, 1448, 1294, 1242, 1053.

Example 33

Trans-4-amino-[(S)-N-[(S)-2-isobutyloxycarbonylamino-3-ethylthio-3-methylbutanoyl]prolyl]aminomethylcyclohexane (Compound No. 17 in Table 1) hydrochloride NMR (CDCl$_3$): 8.31 (br, 3H), 7.18 (t, 1H), 5.62 (d, 1H), 4.58 (d, 1H), 4.34 (d, 1H), 4.00–3.85 (m, 2H), 3.85–3.70 (m, 2H), 3.20–2.90 (m, 3H), 2.70–2.50 (m, 2H), 2.35 (m, 1H), 2.20–1.40 (m, 11H), 1.43 (s, 3H), 1.39 (s, 3H), 1.22 (t, 3H), 0.94 (d, 6H), 1.10–0.90 (m, 2H); IR: 3346, 2962, 2874, 1697, 1643, 1529, 1446, 1294, 1240, 1055.

Example 34

Trans-4-amino-[(S)-N-[(S)-2-isopropoxycarbonylamino-3-ethylthio-3-methylbutanoyl]prolyl]aminomethylcyclohexane (Compound No. 15 in Table 1) hydrochloride NMR (CDCl$_3$): 8.32 (br, 3H), 7.26 (t, 1H), 5.69 (d, 1H), 4.82 (m, 1H), 4.55 (d, 1H), 3.94 (m, 1H), 3.77 (m, 1H), 3.18–2.85 (m, 3H), 2.65–2.45 (m, 2H), 2.31 (m, 1H), 2.20–1.40 (m, 10H), 1.44 (s, 3H), 1.39 (s, 3H), 1.28–1.17 (m, 9H), 1.10–0.90 (m, 2H); IR: 3406, 2978, 2874, 1687, 1637, 1541, 1448, 1255, 1111, 1039.

Example 35

Trans-4-amino-[(S)-N-[(S)-2-butoxycarbonylamino-3-propylthio-3-methyl-butanoyl]prolyl]aminomethylcyclohexane (Compound No. 34 in Table 1) hydrochloride NMR (CDCl$_3$): 8.32 (br, 3H), 7.18 (br, 1H), 5.58 (d, 1H), 4.57 (d, 1H), 4.34 (d, 1H), 4.11 (m, 1H), 3.98 (m, 2H), 3.78 (m, 1H), 3.16–2.94 (m, 3H), 2.50 (m, 2H), 2.36 (m, 1H), 2.18 (m, 2H), 2.00 (m, 4H), 1.84 (m, 2H), 1.58 (m, 7H), 1.48–1.30 (m, 2H), 1.43 (s, 3H), 1.39 (s,3H), 1.10–0.90 (m, 2H), 0.99 (t, 3H), 0.94 (t, 3H); IR: 3428, 3349, 2961, 2936, 1690, 1640, 1535, 1449, 1242, 1065.

Example 36

Trans-4-amino-[(S)-N-[(S)-2-butoxycarbonylamino-3-isopropylthio-3-methylbutanoyl]prolyl]aminomethylcyclohexane (Compound No. 53 in Table 1) hydrochloride NMR (CDCl$_3$): 8.32 (br, 3H), 7.18 (br, 1H), 5.58 (d, 1H), 4.58 (d, 1H), 4.32 (d, 1H), 4.11 (m,1H), 3.97 (m, 2H), 3.75 (m, 1H), 3.10–3.00 (m, 3H), 3.00 (m, 2H), 2.38 (m, 1H), 2.16 (m, 2H), 2.08 (m, 4H), 1.84 (m, 4H), 1.61 (m, 2H), 1.56–1.40 (m, 2H), 1.42 (s, 3H), 1.37 (s, 3H), 1.32 (d, 3H), 1.26 (d, 3H), 1.04–0.90 (m, 2H), 0.94 (t, 3H); IR: 3349, 3341, 2959, 2934, 1690, 1638, 1524, 1449, 1242, 1065.

Example 37

Trans-4-amino-[(S)-N-[(S)-2-butoxycarbonylamino-3-butylthio-3-methyl-butanoyl]prolyl]aminomethylcyclohexane (Compound No. 81 in Table 1) hydrochloride NMR (CDCl$_3$): 8.30 (br, 3H), 7.18 (br, 1H), 5.58 (d, 1H), 4.55 (d, 1H), 4.33 (d, 1H), 4.08 (m, 1H), 4.04–3.86 (m, 2H), 3.70 (m, 1H), 3.12–2.90 (m, 3H), 2.52 (m, 2H), 2.36 (m, 1H), 2.16 (m, 2H), 1.98 (m, 3H), 1.80 (m, 2H), 1.64–1.30 (m, 9H), 1.43 (s, 3H), 1.38 (s, 3H), 1.04–0.90 (m, 2H), 0.94 (t, 3H), 0.91 (t, 3H); IR: 3345, 2959, 2872, 1692, 1640, 1535, 1449, 1242, 1065.

Example 38

Trans-4-amino-[(S)-N-[(S)-2-butoxycarbonylamino-3-isobutylthio-3-methylbutanoyl]prolyl]aminomethylcyclohexane (Compound No. 100 in Table 1) hydrochloride NMR (CDCl3): 8.31 (br, 3H), 7.19 (br, 1H), 5.58 (d, 1H), 4.57 (d, 1H), 4.32 (d, 1H), 4.10 (m, 1H), 3.96 (m, 2H), 3.78

(m, 1H), 3.09 (m, 2H), 2.99 (m, 1H), 2.41 (m, 1H), 2.35 (m, 2H), 2.20 (m, 2H), 1.99 (m, 3H), 1.89–1.75 (m, 3H), 1.62 (m, 3H), 1.58–1.36 (m, 4H), 1.42 (s, 3H), 1.38 (s, 3H), 1.00–0.90 (m, 2H), 0.99 (d, 6H), 0.94 (t, 3H); IR: 3445, 2959, 1686, 1638, 1541, 1449, 1242, 1065.

Example 39

Trans-4-amino-[(S)-N-[(S)-2-pentyloxycarbonylamino-3-isopropylthio-3-methylbutanoyl]prolyl]aminomethylcyclohexane (Compound No. 56 in Table 1) hydrochloride NMR (CDCl$_3$): 8.34 (br, 3H), 7.20 (br, 1H), 5.60 (d, 1H), 4.60 (d, 1H), 4.31 (d, 1H), 4.03 (m, 2H), 4.03 (m, 1H), 3.80 (m, 1H), 3.28–3.06 (m, 4H), 2.46 (m, 1H), 2.28 (m, 2H), 2.06 (m, 4H), 1.92 (m, 4H), 1.70 (m, 4H), 1.62–1.46 (m, 2H), 1.48 (s, 3H), 1.41 (s, 3H), 1.32 (d, 3H), 1.26 (d, 3H), 1.10–1.00 (m, 2H), 0.92 (t, 3H); IR: 3428, 3347, 2957, 2934, 1690, 1640, 1524, 1449, 1240, 1055.

Example 40

Trans-4-amidino-[(S)-N-[(S)-2-propoxycarbonylamino-3-isopropylthio-3-methylbutanoyl]prolyl]aminomethylcyclohexane (Compound No. 410 in Table 1) hydrochloride a) Trans-4-N-benzyloxycarbonylaminomethyl-cyclohexylnitrile To a solution of trans-4-aminomethylcyclohexanecarboxylic acid (25 g, 159 mmol) and sodium carbonate (20 g, 191 mmol) in water (300 ml), benzyloxycarbonyl chloride (27 ml, 190 mmol) was added at 0° C. After stirring was continued for six hours, the mixture was added with 1N hydrochloric acid to adjust its pH to 2, and the deposited white solid was collected by filtration and washed with water, and then dried. The resulting white solid was dissolved in THF (300 ml), and the solution was added with CDI (21 g, 130 mmol) at 0° C. After stirring was continued for three hours, the reaction mixture was added dropwise to a mixture of concentrated aqueous ammonia (50 ml) and THF (150 ml) at 0° C. After stirring for five hours, the solvent was evaporated, and water (500 ml) was added to the residue. The deposited white solid was collected by filtration and washed with water, and then dried.

To a solution of the above-obtained compound in 1,2-dichloroethane (500 ml), thionyl chloride (19 ml, 260 mmol) was added, and then the mixture was heated at an internal temperature of 70° C. After stirring was continued for five hours, the reaction mixture was poured into iced water, and the mixture was neutralized with 1N aqueous sodium hydroxide. The mixture was extracted with chloroform, and the organic layer was washed twice with water and once with saturated brine, and then dried over sodium sulfate. After the solvent was evaporated, the resulting crude product was recrystallized (hexane/ethyl acetate) to obtain the title compound a) (22.8 g, 53%). mp 90–92° C.

b) Trans-4-(S)-prolylaminomethyl-cyclohexylnitrile

The compound obtained in the above a) was dissolved in ethanol (250 ml), and the solution was subjected to catalytic reduction in the presence of palladium black (1g) at ambient temperature under atmospheric pressure. After the completion of the reaction, the catalyst was removed by filtration, and then the solvent was evaporated.

To a solution of (S)-N-benzyloxycarbonylproline (20.7 g, 83 mmol) in THF (150 ml), CDI (13.5 g, 83 mmol) was added at 0° C. After stirring was continued for three hours, the mixture was added with a solution of the compound obtained by the above-described reduction in THF (200 ml) at 0° C. After the mixture was stirred for 12 hours, the solvent was evaporated, and chloroform (400 ml) was added to the resulting residue. The organic layer was washed three times with water and once with saturated brine, and then dried over sodium sulfate. The solvent was evaporated, and the resulting residue was purified by silica gel column chromatography (chloroform/methanol).

The resulting compound was dissolved in ethanol (250 ml), and the solution was subjected to catalytic reduction in the presence of palladium black (1 g) at ambient temperature under atmospheric pressure. After the completion of the reaction, the catalyst was removed by filtration, and the solvent was evaporated to obtain the title compound b) (18.8 g, yield; 95%).

NMR (DMSO-d$_6$): 0.88–1.06 (m, 2H), 1.38–1.52 (m, 3H), 1.68–2.03 (m, 7H), 2.20–2.40 (m, 1H), 2.52–2.67 (m, 1H), 2.80–3.20 (m, 4H), 4.03–4.10 (m, 1H), 7.53 (br, 1H), 8.65–8.70 (m, 1H);

c) Trans-4-[(S)-N-[(S)-2-propoxycarbonylamino-3-isopropylthio-3-methylbutanoyl]-prolyl] aminomethylcyclohexylnitrile To a solution of the compound obtained in the above b) (1.04 g, 4.4 mmol), (S)-2-propoxycarbonylamino-3-isopropylthio-3-methylbutanoic acid (1.20 g, 4.3 mmol) and triethylamine (1.5 g, 14.8 mmol) in dichloromethane (35 ml), a solution of diethyl phosphorocyanidate (DEPC, 0.85 g, 5.3 mmol) in dichloromethane (5 ml) was added dropwise at 0° C. The temperature of the mixture was raised up to room temperature, and stirring was further continued for 24 hours. The reaction mixture was added with water, and the mixture was extracted twice with dichloromethane, and then the organic layer was dried over sodium sulfate. The solvent was evaporated, and the residue was purified by silica gel column chromatography (chloroform/methanol) to obtain the title compound c) (1.77 g, yield; 83%).

NMR (CDCl$_3$): 7.18 (t, 1H), 5.58 (d, 1H), 4.61 (d, 1H), 4.33 (d, 1H), 4.20–3.85 (m, 3H), 3.73 (m, 1H), 3.20–2.90 (m, 3H), 2.45–2.30 (m, 2H), 2.15–1.20 (m, 12H), 1.47 (s, 3H), 1.41 (s, 3H), 1.29 (dd, 6H), 0.95 (t, 3H), 1.10–0.90 (m, 2H).

d) Trans-4-amidino-[(S)-N-[(S)-2-propoxycarbonylamino-3-isopropylthio-3-methyl-butanoyl]prolyl] aminomethylcyclohexane hydrochloride To a solution of the compound obtained in the above c) (0.70 g, 1.42 mmol) in chloroform (2 ml), a saturated solution of hydrogen chloride in ethanol (10 ml) was added at 0° C., and then the mixture was left to stand at 0° C. for 48 hours. The solvent of the reaction mixture was evaporated, and the resulting residue was dissolved in methanol (15 ml), and then the solution was added with ammonium carbonate (1.0 g, 10.4 mmol) at 0° C. The temperature of the mixture was raised up to room temperature, and stirring was continued for six hours, and then the solvent was evaporated. The resulting residue was purified by silica gel column chromatography (chloroform/methanol) to obtain the title compound d) (0.71 g, yield; 92%).

NMR (CDCl$_3$): 8.87 (br, 2H), 8.57 (br, 2H), 7.48(t, 1H), 6.00(d, 1H), 4.59(d, 1H), 4.13 (m, 1H), 4.10–3.90 (m, 2H), 3.85–3.65 (m, 2H), 3.15 (m, 1H), 3.05–2.85 (m, 2H), 2.60 (m, 1H), 2.21 (m, 1H), 2.10–1.40 (m, 11H), 1.48 (s, 3H), 1.38 (s, 3H), 1.28 (dd, 6H), 0.93 (t, 3H), 1.10–0.90 (m, 2H); IR: 3325, 3084, 2930, 2874, 1693, 1637, 1521, 1446, 1240, 1062.

In similar manners to those described above, the compounds of Examples 40–76 set out below were obtained.

Example 41

Trans-4-amidino-[(S)-N-[(S)-2-ethoxycarbonylamino-3-(1'-ethylpropylthio)-3-methylbutanoyl]prolyl]aminomethylcyclohexane (Compound No. 514 in Table 1) hydrochloride NMR (CDCl$_3$): 8.83 (br, 2H), 8.72 (br, 2H), 7.52 (t, 1H), 5.98 (d, 1H), 4.61 (d, 1H), 4.30–4.15 (m, 3H), 4.00 (m, 1H), 3.71 (m, 1H), 3.18 (m, 1H), 2.89 (m, 1H), 2.70–2.50 (m, 2H), 2.24 (m, 1H), 2.10–1.40 (m, 17H), 1.45 (s, 3H), 1.37 (s, 3H), 1.28 (t, 3H), 1.10–0.90 (m, 2H), 0.96 (dt, 6H); IR: 3298, 3063, 2964, 2868, 1685, 1647, 1521, 1444, 1240, 1055.

Example 42

Trans-4-amidino-[(S)-N-[(S)-2-ethoxycarbonylamino-3-propylthio-3-methylbutanoyl]prolyl]aminomethylcyclohexane (Compound No. 393 in Table 1) hydrochloride NMR (CDCl$_3$): 8.76 (br, 2H), 8.69 (br, 2H), 7.52 (t, 1H), 6.06 (d, 1H), 4.58 (d, 1H), 4.38 (d, 1H), 4.50–4.05 (m, 2H), 3.94 (m, 1H), 3.81 (m, 1H), 3.13 (m, 1H), 2.94 (m, 1H), 2.65 (m, 1H), 2.65–2.40 (m, 2H), 2.19 (m, 1H), 2.15–1.40 (m, 12H), 1.43 (s, 3H), 1.37 (s, 3H), 1.27 (t, 3H), 0.99 (t, 3H), 1.10–0.90 (m, 2H) IR: 3296, 3074, 2932, 2872, 1693, 1639, 1523, 1444, 1242, 1055.

Example 43

Trans-4-amidino-[(S)-N-[(S)-2-ethoxycarbonylamino-3-isobutylthio-3-methylbutanoyl]prolyl]aminomethylcyclohexane (Compound No. 452 in Table 1) hydrochloride NMR (CDCl$_3$): 8.76 (br, 2H), 8.72 (br, 2H), 7.55 (t, 1H), 6.04 (d, 1H), 4.59(d, 1H), 4.36 (d, 1H), 4.30–4.05 (m, 2H), 3.96 (m, 1H), 3.77 (m, 1H), 3.06 (m, 1H), 2.96 (m, 1H), 2.62 (m, 1H), 2.50–2.30 (m, 2H), 2.20–1.40 (m, 12H), 1.42 (s, 3H), 1.36 (s, 3H), 1.27 (t, 3H) 0.98 (d, 6H), 1.10–0.90 (m, 2H) IR: 3296, 3086, 2959, 2930, 2870, 1687, 1639, 1527, 1444, 1242, 1055.

Example 44

Trans-4-amidino-[(S)-N-[(S)-2-isopropoxycarbonylamino-3-ethylthio-3-methylbutanoyl]prolyl]aminomethylcyclohexane (Compound No. 378 in Table 1) hydrochloride NMR (CDCl$_3$): 8.78 (br, 2H), 8.61 (br, 2H), 7.59 (t, 1H), 5.83 (d, 1H), 4.82 (m, 1H), 4.57 (d, 1H), 4.39 (d, 1H), 3.93 (m, 1H), 3.90–3.65 (m, 2H), 3.15–2.90 (m, 2H), 2.70–2.45 (m, 4H), 2.30–1.40 (m, 9H), 1.42 (s, 3H), 1.37 (s, 3H), 1.25 (d, 6H), 1.21 (t, 3H), 1.10–0.90 (m, 2H); IR: 3323, 3067, 2930, 2866, 1685, 1639, 1516, 1446, 1242, 1111.

Example 45

Trans-4-amidino-[(S)-N-[(S)-2-isopropoxycarbonylamino-3-isopropylthio-3-methylbutanoyl]prolyl]aminomethylcyclohexane hydrochloride NMR (CDCl3): 8.74 (br, 2H), 8.68 (br, 2H), 7.62 (t, 1H), 5.84 (d, 1H), 4.83 (m, 1H), 4.57 (d, 1H), 4.36 (d, 1H), 3.98 (m, 1H), 3.71 (m, 1H), 3.10–2.90 (m, 3H), 2.62 (m, 1H), 2.50–1.40 (m, 11H), 1.46 (s, 3H), 1.37 (s, 3H), 1.28 (dd, 6H), 1.26 (d, 6H), 1.10–0.90 (m, 2H); IR: 3292, 3092, 2932, 2872, 1685, 1637, 1516, 1446, 1253, 1047.

Example 46

Trans-4-amidino-[(S)-N-[(S)-2-propoxycarbonylamino-3-ethylthio-3-methylbutanoyl]prolyl]aminocyclohexane (Compound No. 377 in Table 1) hydrochloride NMR (CDCl$_3$): 8.78 (br, 2H), 8.65 (br, 2H), 7.54 (t, 1H), 6.06 (d, 1H), 4.60 (d, 1H), 3.98 (d, 1H), 4.20–3.65 (m, 4H), 3.12 (m, 1H), 2.96 (m, 1H), 2.70–2.50 (m, 4H), 2.30–1.40 (m, 12H), 1.43 (s, 3H), 1.37 (s, 3H), 1.21 (t, 3H), 0.94 (t, 3H), 1.10–0.90 (m, 2H); IR: 3288, 3061, 2924, 2876, 1685, 1641, 1520, 1444, 1240, 1062.

Example 47

Trans-4-amidino-[(S)-N-[(S)-2-methoxycarbonylamino-3-ethylthio-3-methylbutanoyl]proly]aminomethylcyclohexane (Compound No. 375 in Table 1) hydrochloride NMR (CDCl$_3$): 8.77 (br, 4H), 7.53 (t, 1H), 6.25 (d, 1H), 4.61 (d, 1H), 4.35 (d, 1H), 3.94 (m, 1H), 3.81 (m, 1H), 3.74 (s, 3H), 3.22 (m, 1H), 2.87 (m, 1H), 2.70–2.40 (m, 3H), 2.20 (m, 1H), 2.10–1.40 (m, 11H), 1.45 (s, 3H), 1.37 (s, 3H), 1.21 (t, 3H), 1.10–0.90 (m, 2H); IR: 3279, 3072, 2932, 2864, 1689, 1639, 1527, 1446, 1242, 1059.

Example 48

Trans-4-amidino-[(S)-N-[(S)-2-methoxycarbonylamino-3-isopropylthio-3-methylbutanoyl]prolyl]aminomethylcyclohexane (Compound No. 419 in Table 1) hydrochloride NMR (CDCl$_3$): 8.84 (br, 2H), 8.77 (br, 2H), 7.49 (t, 1H), 6.17 (d, 1H), 4.62 (d, 1H), 4.35 (d, 1H), 3.99 (m, 1H), 3.75 (s, 3H), 3.70 (m, 1H), 3.24 (m, 1H), 2.96 (m, 1H), 2.87 (m, 1H), 2.53 (m, 1H), 2.23 (m, 1H), 2.10–1.40 (m, 10H), 1.49 (s, 3H), 1.37 (s, 3H), 1.26 (dd, 6H), 1.10–0.90 (m, 2H); IR: 3296, 3072, 2930, 2876, 1689, 1639, 1523, 1446, 1242, 1053.

Example 49

Trans-4-amidino-[(S)-N-[(S)-2-methoxycarbonylamino-3-propylthio-3-methylbutanoyl]prolyl]aminomethylcyclohexane (Compound No. 392 in Table 1) hydrochloride NMR (CDCl$_3$): 8.79 (br, 4H), 7.26 (t, 1H), 6.25 (d, 1H), 4.61 (d, 1H), 4.36 (d, 1H), 4.02 (m, 1H), 3.78 (m, 1H), 3.74 (s, 3H), 3.24 (m, 1H), 2.95 (m, 1H), 2.60 (m, 1H), 2.48 (q, 2H), 2.21 (m, 1H), 2.10–1.40 (m, 12H), 1.44 (s, 3H), 1.37 (s, 3H), 0.99 (t, 3H), 1.10–0.90 (m, 2H); IR: 3314, 3082, 2932, 2872, 1685, 1637, 1524, 1448, 1242, 1055.

Example 50

Trans-4-amidino-[(S)-N-[(S)-2-methoxycarbonylamino-3-isobutylthio-3-methylbutanoyl]prolyl]aminomethylcyclohexane (Compound No. 451 in Table 1) hydrochloride NMR (CDCl$_3$): 8.78 (br, 4H), 7.54 (t, 1H), 6.24 (d, 1H), 4.60 (d, 1H), 4.36 (d, 1H), 3.95 (m, 1H), 3.79 (m, 1H), 3.73 (s, 3H), 3.16 (m, 1H), 2.89 (m, 1H), 2.60 (m, 1H), 2.50–2.30

(m, 2H), 2.22 (m, 1H), 2.10–1.40 (m, 11H), 1.43 (s, 3H), 1.36 (s, 3H), 0.98 (d, 6H), 1.10–0.90 (m, 2H); IR: 3329, 3090, 2934, 2872, 1682, 1637, 1523, 1448, 1242, 1055.

Example 51

Trans-4-amidino-[(S)-N-[(S)-2-ethoxycarbonylamino-3-ethylthio-3-methylbutanoyl]prolyl]aminomethylcyclohexane (Compound No. 376 in Table 1) hydrochloride NMR (CDCl$_3$): 8.81 (br, 2H), 8.72 (br, 2H), 7.58 (t, 1H), 6.05 (d, 1H), 4.61 (d, 1H), 4.38 (d, 1H), 4.23–4.05 (m, 2H), 3.94 (m, 1H), 3.77 (m, 1H), 3.13 (m, 1H), 2.99 (m, 1H), 3.70–3.50 (m, 3H), 2.19 (m, 1H), 2.10–1.40 (m, 10H), 1.44 (s, 3H), 1.37 (s, 3H), 1.28 (t, 3H), 1.22 (t, 3H), 1.10–0.90 (m, 2H); IR: 3323, 3076, 2932, 2870, 1685, 1637, 1521, 1444, 1242, 1059.

Example 52

Trans-4-amidino-[(S)-N-[(S)-2-ethoxycarbonylamino-3-cyclopentylthio-3-methylbutanoyl]prolyl]aminomethylcyclohexane (Compound No. 499 in Table 1) hydrochloride NMR (CDCl$_3$): 8.84 (br, 2H), 8.71 (br, 2H), 7.54 (t, 1H), 6.01 (d, 1H), 4.61 (d, 1H), 4.34 (d, 1H), 4.25–4.10 (m, 2H), 3.96 (m, 1H), 3.74 (m, 1H), 3.25–3.00 (m, 2H), 2.91 (m, 1H), 2.59 (m, 1H), 2.21 (m, 1H), 2.20–1.40 (m, 18H), 1.47 (s, 3H), 1.37 (s, 3H), 1.29 (t, 3H), 1.10–0.90 (m, 2H); IR: 3312, 3070, 2937, 2868, 1689, 1637, 1521, 1446, 1242, 1055.

Example 53

Trans-4-amidino-[(S)-N-[(S)-2-ethoxycarbonylamino-3-phenylmethylthio-3-methylbutanoyl]prolyl]aminomethylcyclohexane (Compound No. 529 in Table 1) hydrochloride NMR (CDCl$_3$): 8.83 (br, 2H), 8.69 (br, 2H), 7.49 (t, 1H), 7.38–7.20 (m, 5H), 5.97 (d, 1H), 4.60 (d, 1H), 4.21 (d, 1H), 4.20–4.15 (m, 2H), 3.83 (m, 1H), 3.78 (s, 2H), 3.62 (m, 1H), 3.11 (m, 1H), 2.88 (m, 1H), 2.54 (m, 1H), 2.18 (m, 1H), 2.15–1.40 (m, 10H), 1.47 (s, 3H), 1.37 (s, 3H), 1.28 (t, 3H) 1.10–0.90 (m, 2H); IR: 3315, 3062, 2932, 2866, 1685, 1639, 1518, 1446, 1240, 1055.

Example 54

Trans-4-amidino-[(S)-N-[(S)-2-propoxycarbonylamino-3-cyclopentylthio-3-methylbutanoyl]prolyl]aminomethylcyclohexane (Compound No. 500 in Table 1) hydrochloride NMR (CDCl$_3$): 8.79 (br, 2H), 8.70 (br, 2H), 7.55 (t, 1H), 6.03 (d, 1H), 4.60 (d, 1H), 4.36 (d, 1H), 4.20–3.92 (m, 3H), 3.75 (m, 1H), 3.20–2.80 (m, 3H), 2.62 (m, 1H), 2.20 (m, 1H), 2.10–1.40 (m, 20H), 1.46 (s, 3H), 1.38 (s, 3H), 0.94 (t, 3H), 1.10–0.90 (m, 2H); IR: 3283, 3080, 2935, 2870, 1685, 1647, 1521, 1446, 1238, 1060.

Example 55

Trans-4-amidino-[(S)-N-[(S)-2-propoxycarbonylamino-3-propylthio-3-methylbutanoyl]prolyl]aminomethylcyclohexane (Compound No. 394 in Table 1) hydrochloride NMR (CDCl$_3$): 8.78 (br, 2H), 8.69 (br, 2H), 7.57 (t, 1H), 6.05 (d, 1H), 4.59 (d, 1H), 4.36 (d, 1H), 4.09 (m, 1H), 4.05–3.90 (m, 2H), 3.79 (m, 1H), 3.11 (m, 1H), 2.92 (m, 1H), 2.62 (m, 1H), 2.60–2.45 (m, 2H), 2.19 (m, 1H), 2.10–1.40 (m, 14H), 1.43 (s, 3H), 1.37 (s, 3H), 0.99 (t, 3H), 0.94 (t, 3H), 1.10–0.90 (m, 2H); IR: 3314, 3084, 2937, 2874, 1689, 1637, 1523, 1444, 1238, 1062.

Example 56

Trans-4-amidino-[(S)-N-[(S)-2-propoxycarbonylamino-3-isobutylthio-3-methylbutanoyl]prolyl]aminomethylcyclohexane (Compound No. 453 in Table 1) hydrochloride NMR (CDCl$_3$): 8.74 (br, 4H), 7.58 (t, 1H), 6.06 (d, 1H), 4.58 (d, 1H), 4.38 (d, 1H), 4.18–3.90 (m, 3H), 3.78 (m, 1H), 3.08 (m, 1H), 2.97 (m, 1H), 2.63 (m, 1H), 2.50–2.30 (m, 2H), 2.20–1.40 (m, 14H), 1.42 (s, 3H), 1.37 (s, 3H), 0.98 (d, 6H), 0.94 (t, 3H), 1.10–0.90 (m, 2H) IR: 3335, 3086, 2926, 2874, 1685, 1637, 1521, 1448, 1242, 1062.

Example 57

Trans-4-amidino-[(S)-N-[(S)-2-propoxycarbonylamino-3-butylthio-3-methylbutanoyl]prolyl]aminomethylcyclohexane (Compound No. 435 in Table 1) hydrochloride NMR (CDCl$_3$): 8.78 (br, 2H), 8.68 (br, 2H), 7.53 (t, 1H), 6.05 (d, 1H), 4.59 (d, 1H), 4.08 (m, 1H), 4.05–3.90 (m, 2H), 3.77 (m, 1H), 3.13 (m, 1H), 2.92 (m (m, 1H), 2.50–2.45 (m, 2H), 2.20 (m, 1H), 2.10–1.40 (m, 16H), 1.43 (s, 3H), 1.37 (s, 3H), 0.94 (t, 3H), 0.91 (t, 3H), 1.10–0.90 (m, 2H); IR: 3269, 3067, 2932, 2863, 1685, 1635, 1521, 1446, 1238, 1062.

Example 58

Trans-4-amidino-[(S)-N-[(S)-2-propoxycarbonylamino-3-cyclohexyl-methylthio-3-methylbutanoyl]prolyl]aminomethylcyclohexane (Compound No. 554 in Table 1) hydrochloride NMR (CDCl$_3$): 8.83 (br, 2H), 8.65 (br, 2H), 7.49 (t, 1H), 6.01 (d, 1H), 4.58 (d, 1H), 4.34 (d, 1H), 4.20–3.95 (m, 3H), 3.78 (m, 1H), 3.13 (m, 1H), 2.92 (m, 1H), 2.61 (m, 1H), 2.50–2.30 (m, 2H), 2.29 (m, 1H), 2.02 (m, 2H), 1.95–1.10 (m, 21H), 1.42 (s, 3H), 1.36 (s, 3H), 0.95 (t, 3H), 1.10–0.90 (m, 2H); IR: 3346, 3088, 2926, 2852, 1693, 1655, 1543, 1523, 1448, 1238, 1062.

Example 59

Trans-4-amidino-[(S)-N-[(S)-2-propoxycarbonylamino-3-cyclobutylthio-3-methylbutanoyl]prolyl]aminomethylcyclohexane (Compound No. 469 in Table 1) hydrochloride NMR (CDCl$_3$): 8.78 (br, 2H), 8.71 (br, 2H), 7.56 (t, 1H), 6.03 (d, 1H), 4.60 (d, 1H), 4.33 (d, 1H), 4.20–3.90 (m, 3H), 3.77 (m, 1H), 3.55 (m, 1H), 3.12 (m, 1H), 2.94 (m, 1H), 2.62 (m, 1H), 2.40–2.25 (m, 2H), 2.20–1.40 (m, 17H), 1.40 (s, 3H), 1.33 (s, 3H), 0.94 (t, 1H), 1.10–0.90 (m, 2H); IR: 3296, 3072, 2932, 2874, 1685, 1639, 1521, 1444, 1240, 1060.

Example 60

Trans-4-amidino-[(S)-N-[(S)-2-propoxycarbonylamino-3-(1'-ethylpropylthio)-3-methylbutanoyl]prolyl]aminomethylcyclohexane (Compound No. 515 in Table 1) hydrochloride NMR (CDCl$_3$): 8.81 (br, 2H), 8.75 (br, 2H), 7.52 (t, 1H), 5.99 (d, 1H), 4.60 (d, 1H), 4.27 (d, 1H), 4.20–3.95 (m, 3H), 3.70 (m, 1H), 3.13 (m, 1H), 2.90 (m, 1H), 2.70–2.45 (m, 2H), 2.21 (m, 2H), 2.10–1.40 (m, 19H), 1.45 (s, 3H), 1.37 (s, 3H), 1.10–0.90 (m, 8H); IR: 3329, 3067, 2934, 2878, 1685, 1637, 1521, 1448, 1238, 1060.

Example 61

Trans-4-amidino-[(S)-N-[(S)-2-isobutyloxycarbonylamino-3-cyclopentyl-thio-3-methylbutanoyl]prolyl]aminomethylcyclohexane (Compound No. 503 in Table 1) hydrochloride NMR (CDCl$_3$): 8.82 (br, 2H), 8.64 (br, 2H), 7.54 (t, 1H), 6.03 (d, 1H), 4.59 (d, 1H), 4.37 (d, 1H), 4.05–3.90 (m, 2H), 3.90–3.70 (m, 2H), 3.15–3.05 (m, 2H), 2.92 (m, 1H), 2.62 (m, 1H), 2.23 (m, 1H), 2.10–1.40 (m, 19H), 1.47 (s, 3H), 1.38 (s, 3H), 0.94 (d, 6H), 1.10–0.90 (m, 2H); IR: 3279, 3082, 2961, 2872, 1685, 1643, 1518, 1446, 1238, 1053.

Example 62

Trans-4-amidino-[(S)-N-[(S)-2-isobutyloxycarbonylamino-3-isopropylthio-3-methylbutanoyl]prolyl]aminomethylcyclohexane (Compound No. 413 in Table 1) hydrochloride NMR (CDCl$_3$): 8.78 (br, 2H), 8.69 (br, 2H), 7.56 (t, 1H), 6.06 (d, 1H), 4.59 (d, 1H), 4.38 (d, 1H), 4.05–3.90 (m, 2H), 3.90–3.85 (m, 2H), 3.09 (m, 1H), 3.08–2.85 (m, 2H), 2.62 (m, 1H), 2.17 (m, 1H), 2.10–1.40 (m, 11H), 1.48 (s, 3H), 1.38 (s, 3H), 1.29 (dd, 6H), 0.93 (d, 6H), 1.10–0.90 (m, 2H); IR: 3271, 3069, 2934, 2876, 1685, 1641, 1518, 1448, 1238, 1053.

Example 63

Trans-4-amidino-[(S)-N-[(S)-2-propoxycarbonylamino-3-(3'-methylbutylthio)-3-methylbutanoyl]prolyl]aminomethylcyclohexane (Compound No. 572 in Table 1) hydrochloride NMR (CDCl$_3$): 8.80 (br, 2H), 8.67 (br, 2H), 7.49 (t, 1H), 6.04 (d, 1H), 4.59 (d, 1H), 4.36 (d, 1H), 4.20–3.95 (m, 3H), 3.73 (m, 1H), 3.15 (m, 1H), 2.93 (m, 1H), 2.70–2.45 (m, 3H), 2.20 (m, 1H), 2.10–1.40 (m, 15H), 1.44 (s, 3H), 1.37 (s, 3H), 0.94 (t, 3H), 0.90 (d, 6H), 1.10–0.90 (m, 2H); IR: 3314, 3074, 2930, 2872, 1685, 1637, 1523, 1240, 1062.

Example 64

Trans-4-amidino-[(S)-N-[(S)-2-isobutyloxycarbonylamino-3-propylthio-3-methylbutanoyl]prolyl]aminomethylcyclohexane (Compound No. 397 in Table 1) hydrochloride NMR (CDCl$_3$): 8.77 (br, 2H), 8.68 (br, 2H), 7.56 (t, 1H), 6.07 (d, 1H), 4.58 (d, 1H), 4.39 (d, 1H), 4.05–3.90 (m, 2H), 3.90–3.70 (m, 2H), 3.10 (m, 1H), 2.95 (m, 1H), 2.65 (m, 1H), 2.60–2.40 (m, 2H), 2.18 (m, 1H), 2.10–1.40 (m, 13H), 1.43 (s, 3H), 1.37 (s, 3H), 0.99 (t, 3H), 0.94 (d, 6H), 1.10–0.90 (m, 2H); IR: 3314, 3069, 2935, 2874, 1685, 1637, 1521, 1448, 1240, 1053.

Example 65

Trans-4-amidino-[(S)-N-[(S)-2-isobutyloxycarbonylamino-3-isobutylthio-3-methylbutanoyl]prolyl]aminomethylcyclohexane (Compound No. 456 in Table 1) hydrochloride NMR (CDCl$_3$): 8.76 (br, 2H), 8.69 (br, 2H), 7.56 (t, 1H), 6.06 (d, 1H), 4.59 (d, 1H), 4.37 (d, 1H), 4.05–3.90 (m, 2H), 3.90–3.70 (m, 2H), 3.08 (m, 1H), 2.96 (m, 1H), 2.62 (m, 1H), 2.50–2.30 (m, 2H), 2.17 (m, 1H), 2.10–1.40 (m, 12H), 1.42 (s, 3H), 1.37 (s, 3H), 0.99 (d, 6H), 0.94 (d, 6H), 1.10–0.90 (m, 2H); IR: 3306, 3067, 2961, 2874, 1685, 1645, 1518, 1321, 1240, 1053.

Example 66

Trans-4-amidino-[(S)-N-[(S)-2-isobutyloxycarbonylamino-3-ethylthio-3-methylbutanoyl]prolyl]aminomethylcyclohexane (Compound No. 380 in Table 1) hydrochloride NMR (CDCl$_3$): 8.74 (br, 2H), 8.70 (br, 2H), 7.58 (t, 1H), 6.08 (d, 1H), 4.58 (d, 1H), 4.41 (d, 1H), 4.05–3.90 (m, 2H), 3.90–3.70 (m, 2H), 3.07 (m, 1H), 2.97 (m, 1H), 2.75–2.50 (m, 3H), 2.20–1.40 (m, 12H), 1.43 (s, 3H), 1.37 (s, 3H), 1.21 (t, 3H), 0.93 (d, 6H), 1.10–0.90 (m, 2H); IR: 3279, 3076, 2934, 2874, 1695, 1637, 1521, 1446, 1240, 1055.

Example 67

Trans-4-amidino-[(S)-N-[(S)-2-butoxycarbonylamino-3-isobutylthio-3-methylbutanoyl]prolyl]aminomethylcyclohexane (Compound No. 455 in Table 1) hydrochloride NMR (CDCl$_3$): 8.78 (br, 2H), 8.66 (br, 2H), 7.55 (br, 1H), 5.97 (d, 1H), 4.57 (d, 1H), 4.38 (d, 1H), 4.14 (m, 1H), 3.99 (m, 1H), 3.80 (m, 1H), 3.07 (m, 1H), 2.99 (m, 1H) 2.64 (m, 1H), 2.39 (m, 2H), 2.22 (m, 1H), 2.18–1.74 (m, 8H), 1.62 (m, 4H), 1.50–1.33 (m, 2H), 1.42 (s, 3H), 1.37 (s, 3H), 1.08–0.95 (m, 2H), 0.98 (d, 6H), 0.93 (t, 3H); IR: 3316, 3084, 2959, 2932, 1686, 1638, 1522, 1449, 1242, 1065.

Example 68

Trans-4-amidino-[(S)-N-[(S)-2-butoxycarbonylamino-3-butylthio-3-methylbutanoyl]prolyl]aminomethylcyclohexane (Compound No. 437 in Table 1) hydrochloride NMR (CDCl$_3$): 8.72 (br, 4H), 7.57 (br, 1H), 5.99 (d, 1H), 4.56 (d, 1H), 4.40 (d, 1H), 4.12 (m, 1H), 3.97 (m, 2H), 3.73 (m, 1H), 3.02 (m, 2H), 2.68–2.44 (m, 4H), 2.51 (m, 1H), 2.22 (m, 1H), 2.08–1.70 (m, 8H), 1.64–1.59 (m, 3H), 1.54–1.49 (m, 3H), 1.44–1.34 (m, 2H), 1.41 (s, 3H), 1.37 (s, 3H), 1.10–0.96 (m, 2H), 0.93 (t, 3H), 0.91 (t, 3H); IR: 3299, 3084, 2959, 2932, 1686, 1638, 1520, 1449, 1242, 1065.

Example 69

Trans-4-amidino-[(S)-N-[(S)-2-butoxycarbonylamino-3-isopropylthio-3-methylbutanoyl]prolyl]aminomethylcyclohexane (Compound No. 412 in Table 1) hydrochloride NMR (CDCl$_3$): 8.76 (br, 2H), 8.69 (br, 2H), 7.57 (br, 1H), 5.97 (d, 1H), 4.58 (d, 1H), 4.38 (d, 1H), 4.13 (m, 1H), 3.98 (m, 2H), 3.78 (m, 1H), 3.10–3.00 (m, 2H), 2.99 (m, 1H), 2.64 (m, 1H), 2.35–2.00 (m, 7H), 2.00–1.90 (m, 4H), 1.62 (m, 4H), 1.47 (s, 3H), 1.38 (s, 3H), 1.31 (d, 3H), 1.26 (d, 3H), 1.10–1.00 (m, 2H), 0.93 (t, 3H); IR: 3328, 3079, 2961, 2932, 1686, 1644, 1518, 1449, 1242, 1065.

Example 70

Trans-4-amidino-[(S)-N-[(S)-2-butoxycarbonylamino-3-propylthio-3-methylbutanoyl]prolyl]aminomethylcyclohexane (Compound No. 396 in Table 1) hydrochloride NMR (CDCl$_3$): 8.76 (br, 2H), 8.67 (br, 2H), 7.56 (br, 1H), 5.98 (d, 1H), 4.56 (d, 1H), 4.39 (d, 1H), 4.13 (m, 1H), 3.98

(m, 2H), 3.80 (m, 1H), 3.00 (m, 2H), 2.61 (m, 1H), 2.50 (m, 2H), 2.30–1.78 (m, 10H), 1.55 (m, 5H), 1.42 (s, 3H), 1.41–1.32 (m, 2H), 1.37 (s, 3H), 1.04–0.88 (m, 2H), 0.99 (t, 3H), 0.93 (t, 3H); IR: 3318, 3084, 2963, 2934, 1686, 1642, 1518, 1449, 1242, 1065.

Example 71

Trans-4-amidino-[(S)-N-[(S)-2-isopropoxycarbonylamino-3-cyclopentylthio-3-methylbutanoyl]prolyl]aminomethylcyclohexane (Compound No. 501 in Table 1) hydrochloride NMR (CDCl$_3$): 8.77 (br, 2H), 8.64 (br, 2H), 7.59 (br, 1H), 5.80 (d, 1H), 4.84 (m, 1H), 4.57 (d, 1H), 4.38 (d, 1H), 3.96 (m, 1H), 3.78 (m, 1H), 3.06 (m, 1H), 3.01 (m, 1H), 2.62 (m, 1H), 1H), 2.19 (m, 2H), 2.03 (m, 9H), 1.83 (m, 2H), 1.66 (m, 2H), 1.66 (m, 2H), 1.55 (m, 4H), 1.45 (s, 3H), 1.37 (s, 3H), 1.25 (d, 6H), 1.00 (m, 2H); IR: 3329, 3086, 2936, 1686, 1638, 1510, 1149, 1244, 1111.

Example 72

Trans-4-amidino-[(S)-N-[(S)-2-isopropoxycarbonylamino-3-isobutylthio-3-methylbutanoyl]prolyl]aminomethylcyclohexane (Compound No. 454 in Table 1) hydrochloride NMR (CDCl$_3$): 8.78 (br, 2H), 8.63 (br, 2H), 7.59 (br, 1H), 5.80 (d, 1H), 4.84 (m, 1H), 4.57 (d, 1H), 4.37 (d, 1H), 3.95 (m, 1H), 3.79 (m, 1H), 3.02 (m, 2H), 2.62 (m, 1H), 2.40 (m, 2H), 2.26–1.92 (m, 8H), 1.90–1.78 (m, 4H), 1.41 (s, 3H), 1.36 (s, 3H), 1.25 (d, 6H), 1.10–1.00 (m, 2H), 0.98 (d, 6H); IR: 3318, 2961, 2932, 1686, 1642, 1514, 1244, 1111.

Example 73

Trans-4-amidino-[(S)-N-[(S)-2-isopropoxycarbonylamino-3-butylthio-3-methylbutanoyl]prolyl]aminomethylcyclohexane (Compound No. 436 in Table 1) hydrochloride NMR (CDCl$_3$): 8.78 (br, 2H), 8.61 (br, 2H), 7.58 (br, 1H), 5.80 (d, 1H), 4.83 (m, 1H), 4.56 (d, 1H), 4.38 (d, 1H), 3.95 (m, 1H), 3.77 (m, 1H), 3.02 (m, 12H), 2.70–2.44 (m, 3H), 2.24 (m, 1H), 2.16–1.80 (m, 7H), 1.72 (m, 2H), 1.52 (m, 3H), 1.41 (s, 3H), 1.39 (m, 2H), 1.36 (s, 3H), 1.25 (d, 3H), 1.08 (m, 2H), 0.91 (t, 3H); IR: 3314, 2961, 2932, 1684, 1640, 1516, 1447, 1252, 1111.

Example 74

Trans-4-amidino-[(S)-N-[(S)-2-isopropoxycarbonylamino-3-propylthio-3-methylbutanoyl]prolyl]aminomethylcyclohexane (Compound No. 395 in Table 1) hydrochloride NMR (CDCl$_3$): 8.88 (br, 2H), 8.54 (br, 2H), 7.55 (br, 1H), 5.80 (d, 1H), 4.84 (m, 1H), 4.55 (d, 1H), 4.38 (d, 1H), 3.93 (m, 1H), 3.78 (m, 1H), 3.00 (m, 2H), 2.64–2.42 (m, 3H), 2.30–1.86 (m, 9H), 1.55 (m, 4H), 1.41 (s, 3H), 1.37 (s, 3H), 1.26 (d, 3H), 1.24 (d, 3H), 1.00–0.90 (m, 2H), 0.99 (t, 3H); IR: 3329, 2973, 2932, 1686, 1638, 1522, 1449, 1246, 1111.

Example 75

Trans-4-amidino-[(S)-N-[(S)-2-isopropoxycarbonylamino-3-phenylmethylthio-3-methylbutanoyl]prolyl]aminomethylcyclohexane (Compound No. 531 in Table 1) hydrochloride NMR (CDCl$_3$): 8.75 (br, 2H), 8.63 (br, 2H), 7.56 (br, 1H), 7.33–7.22 (m, 5H), 5.81 (d, 1H), 4.82 (m, 1H), 4.56 (d, 1H), 4.31 (d, 1H), 3.82–3.60 (m, 2H), 3.78 (s, 1H), 3.77 (s, 1H), 2.99 (m, 2H), 2.80 (m, 1H), 2.18 (m, 1H), 2.07–1.76 (m, 7H), 1.66 (m, 2H), 1.45 (s, 3H), 1.38 (s, 3H), 1.26 (d, 3H), 1.24 (d, 3H), 0.98 (m, 2H); IR: 3329, 3084, 2980, 2932, 1686, 1647, 1508, 1451, 1242, 1111.

Example 76

Trans-4-amidino-[(S)-N-[(S)-2-butoxycarbonylamino-3-phenylmethylthio-3-methylbutanoyl]prolyl]aminomethylcyclohexane (Compound No. 532 in Table 1) hydrochloride NMR (CDCl$_3$): 8.76 (br, 2H), 8.65 (br, 2H), 7.53 (br, 1H), 7.33–7.21 (m, 5H), 5.97 (d, 1H), 4.57 (d, 1H), 4.31 (d, 1H), 4.11 (m, 1H), 4.01 (m, 1H), 3.86–3.76 (m, 1H), 3.78 (s, 1H), 3.77 (s, 1H), 3.65 (m, 1H), 3.06 (m, 1H), 2.95 (m, 1H), 2.56 (m, 1H), 2.24–1.76 (m, 10H), 1.62 (m, 3H), 1.46 (s, 3H), 1.42–1.35 (m, 2H), 1.39 (s, 3H), 1.04–0.91 (m, 2H), 0.93 (t, 3H); IR: 3337, 3086, 2961, 2934, 1686, 1638, 1522, 1451, 1242, 713.

Test Example 1

Measurement of Thrombin Activity i) Method for Measuring Inhibition of Hydrolysis of Synthesized Substrate (S-2238)

S-2238 (Kabi) was dissolved in Tris/HCl buffer (pH 8.3) to prepare a solution of S-2238at a concentration of 80 $\mu$M in 0.4 M Tris/HCl. To 175 $\mu$l of this solution was added 515 $\mu$l of an aqueous solution of the compound of the present invention and the mixture was incubated at 37° C. for one minute, and then the mixture was mixed with 10 $\mu$l of a 4.4 unit/ml solution of bovine thrombin (Mochida). The rate of hydrolysis reaction of the substrate was determined by detecting alteration of absorbance at 405 nm at 37° C. The concentration of the inhibitor (the compound of the present invention) which gave half of the absorbance value of a sample without the inhibitor was determined as I$_{50}$ ($\mu$M).

ii) Method for Measuring Inhibition of Rat Plasma Coagulation

The compound of the present invention was dissolved in water or physiological saline in a total volume of 0.1 ml, and then the solution was mixed with 0.1 ml of rat plasma and the mixture was incubated at 37° C. for 30 seconds. The reaction mixture was mixed with 0.1 ml of 8 unit/ml solution of bovine thrombin (Mochida) was, and the coagulation time was measured at 37° C. The concentration of the inhibitor (the compound of the present invention) which doubled the coagulation time of a sample without the inhibitor was determined as I$_{50}$ ($\mu$M).

iii) Method for Measuring Antithrombotic Activity in Rat Plasma after Oral Administration The compound of the present invention in the amount of 30 mg/kg was orally administered as an aqueous solution or a suspension to rats starved overnight using an oral tube.

After one hour and three hours, 2 ml of blood was collected from abdominal large vein, and antithrombotic activity in plasma was measured by the method described in the above ii). The values were compared with the result obtained by using blood of a rat not administered with the inhibitor (the compound of the present invention), and prolonging effects on coagulation time were indicated as relative values representing rates of prolongation of thrombin time based on a control as being 1.

Test Example 2

Measurement of Antitrypsin Activity i) Method for Measuring Inhibition of Hydrolysis of Synthesized Substrate (S-2222)

S-2222 (Kabi) was dissolved in Tris/HCl buffer (pH 8.3) to prepare a solution of S-2222 at a concentration of 400 $\mu$M in 0.4 M Tris/HCl. To 175 $\mu$l of this solution was added 515 $\mu$l of an aqueous solution of the compound of the present invention and the mixture was incubated at 37° C. for one minute. The reaction mixture was then mixed with 10 $\mu$l of 1 or 2 mg/ml solution of bovine trypsin (Sigma). The rate of hydrolysis reaction of the substrate was determined by detecting alteration of absorbance at 405 nm at 37° C. The concentration of the an inhibitor (the compound of the present invention) which gave the half of the absorbance value of a sample without the inhibitor was determined as $I_{50}$ ($\mu$M).

The results obtained by the aforementioned Test Examples 1 and 2 are shown in the Table 2 below.

TABLE 2

| Example No. | Antithrombin activity $I_{50}$ ($\mu$M) Synthesized substrate method | Antithrombin activity $I_{50}$ ($\mu$M) Rat plasma method | Antitrypsin activity $I_{50}$ ($\mu$M) | Thrombin time prolongation ratio upon oral administration 1 hour | Thrombin time prolongation ratio upon oral administration 3 hours |
|---|---|---|---|---|---|
| 1 | 0.045 | 0.044 | 41 | 2.16 | 10.36 |
| 2 | 0.051 | 0.057 | 48 | 1.46 | 10.31 |
| 3 | 0.091 | 0.068 | 38 | 3.19 | 2.80 |
| 4 | 0.070 | 0.048 | 52 | 1.84 | 3.72 |
| 5 | 0.14 | 0.11 | 33 | | |
| 6 | 0.080 | 0.082 | 32 | | |
| 7 | 0.13 | | 27 | | |
| 8 | 0.024 | | 7.5 | | |
| 9 | | 0.29 | 68 | | |
| 10 | | 0.10 | 32 | | 2.89 |
| 11 | | 0.097 | 31 | | 1.67 |
| 12 | | 0.081 | 37 | | 5.98 |
| 13 | | 0.076 | 23 | | 6.13 |
| 14 | | 0.079 | 22 | | 2.79 |
| 15 | | 0.36 | 126 | | 1.29 |
| 16 | | 0.069 | 21 | | 5.92 |
| 17 | | 0.089 | 29 | | 4.02 |
| 18 | | 0.11 | 33 | | 4.09 |
| 19 | | 0.14 | 38 | | 3.91 |
| 20 | | 0.57 | 71 | | 1.36 |
| 21 | | 0.11 | 22 | | 5.46 |
| 22 | | 0.068 | 15 | | 4.13 |
| 23 | | 0.48 | 134 | | 1.36 |
| 24 | | 0.095 | 27 | | 6.07 |
| 25 | | 0.14 | 41 | | 3.26 |
| 26 | | 0.12 | 35 | | 3.10 |
| 27 | | 0.086 | 34 | | 2.32 |
| 28 | | 0.081 | 25 | | 2.19 |
| 29 | | 0.070 | 31 | | 3.40 |
| 30 | | 0.22 | 62 | | 2.56 |
| 31 | | 0.078 | 24 | | 5.21 |
| 32 | | 0.10 | 28 | | 2.92 |
| 33 | | 0.093 | 30 | | 4.77 |
| 34 | 0.074 | 0.068 | 29 | 2.35 | 7.22 |
| 35 | | 0.11 | 31 | | 3.76 |
| 36 | | 0.074 | 30 | | 4.11 |
| 37 | | 0.16 | 34 | | 3.21 |
| 38 | | 0.10 | 24 | | 4.41 |
| 39 | | 0.084 | 32 | | 4.90 |
| 40 | | 0.054 | 6.4 | | |
| 41 | | 0.073 | 6.6 | | |
| 42 | | | 6.8 | | |
| 43 | | 0.092 | 7.4 | | |
| 44 | | 0.076 | 12 | | |
| 45 | | 0.072 | | | |
| 46 | | 0.072 | | | |
| 47 | | 0.14 | 6.8 | | |
| 48 | | 0.11 | 8.5 | | |
| 49 | | 0.14 | 4.2 | | |
| 50 | | 0.13 | 6.6 | | |

Industrial Applicability

The penicillaminamide derivatives of the present invention and salts thereof have potent inhibitory activity against thrombin and excellent oral absorbability. Therefore, they are useful as orally available antithrombotic agents, i.e., anticogulants.

What is claimed is:

1. A compound represented by the following general formula (I) or a salt thereof, or a hydrate thereof or a salt thereof, or a hydrate thereof or a solvate thereof:

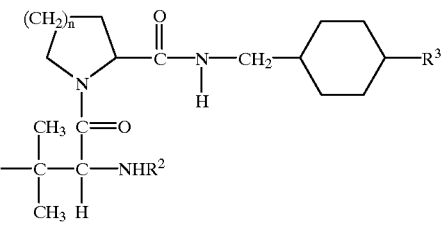

wherein:

n represents 1 or 2;

$R^1$ represents a $C_1$–$C_{10}$ alkyl group which may be substituted with a $C_3$–$C_{10}$ cycloalkyl group or carboxyl group, a $C_6$–$C_{10}$ aryl group which may be substituted, a $C_3$–$C_{10}$ cycloalkyl group which may be substituted, or $C_7$–$C_{12}$ aralkyl group which may be substituted;

$R^2$ represents hydrogen atom, a $C_1$–$C_{10}$ alkyl group, a $C_7$–$C_{12}$ aralkyl group which may be substituted, —COR$^4$ (wherein R$^4$ represents hydrogen atom, a $C_1$–$C_{10}$ alkyl group, a $C_1$–$C_{10}$ alkoxy group, an $C_6$–$C_{10}$ aryl group which may be substituted, a $C_6$–$C_{10}$ aryloxy group which may be substituted, a $C_3$–$C_{10}$ cycloalkyl group which may be substituted, a $C_3$–$C_{10}$ cycloalkyloxy group which may be substituted, a $C_7$–$C_{12}$ aralkyl group which may be substituted, or a $C_7$–$C_{12}$ aralkyloxy group), or —SO$_2$R$^5$ (where R$^5$ represents a $C_1$–$C_{10}$ alkyl group, a $C_6$–$C_{10}$ aryl group which may be substituted, a $C_3$–$C_{10}$ cycloalkyl group which may be substituted, or a $C_7$–$C_{12}$ aralkyl group which may be substituted), and $R^3$ represents amino group or amidino group, provided that the following compounds:

the compound wherein $R^1$ represents methyl group, $R^2$ represents ethoxycarbonyl group, $R^3$ represents amino group, and n represents 1;

the compound wherein $R^1$ represents methyl group, $R^2$ represents methylsulfonyl group, $R^3$ represents amino group, and n represents 1;

the compound wherein $R^1$ represents ethyl group, $R^2$ represents methylsulfonyl group, $R^3$ represents amino group, and n represents 1; and the compound wherein $R^1$ represents isopropyl group, $R^2$ represents ethoxycarbonyl group, $R^3$ represents amidino group, and n represents 1 are excluded.

2. The compound or the salt thereof, or the hydrate thereof or the solvate thereof according to claim 1, wherein at least one of the groups which may be substituted comprises a substituent selected from the group consisting of a $C_1C_6$ alkyl group, a $C_1-C_6$ haloalkyl group, a $C_1-C_6$ alkoxy group, hydroxyl group, carboxyl group, a $C_2-C_7$ carboxyalkyl group, a $C_2-C_7$ carboxyalkyloxy group, a $C_2-C_7$ acyloxy group, a $C_2-C_7$ alkoxycarbonyl group, a $C_2-C_7$ alkoxycarbonyloxy group, a $C_8-C_{10}$ aralkyloxycarbonyl group, a $C_7-C_9$ alkoxycarbonylalkoxy group, and a halogen atom.

3. The compound or the salt thereof, or the hydrate thereof or the solvate thereof according to claim 1, wherein $R^1$ represents a $C_4-C_{10}$ alkyl group, a $C_6-C_{10}$ aryl group which may be substituted, a $C_3-C_{10}$ cycloalkyl group which may be substituted, or a $C_7-C_{12}$ aralkyl group which may be substituted, and $R^3$ represents amidino group.

4. The compound or the salt thereof, or the hydrate thereof or the solvate thereof according to claim 1, wherein $R^3$ represents amino group.

5. The compound or the salt thereof, or the hydrate thereof or the solvate thereof according to claim 1, wherein $R^2$ represents hydrogen atom, a $C_1-C_{10}$ alkyl group, a $C_7-C_{12}$ aralkyl group which may be substituted, or —$COR^4$ wherein $R^4$ is the same as that defined above.

6. The compound or the salt thereof, or the hydrate thereof or the solvate thereof according to claim 1, wherein $R^2$ represents —$COR^4$ wherein $R^4$ represents a $C_{10}$ alkyl group, a $C_1-C_{10}$ alkoxy group, a $C_6-C_{10}$ aryl group which may be substituted, a $C_6-C_{10}$ aryloxy group which may be substituted, a $C_3-C_{10}$ cycloalkyl group which may be substituted, a $C_3-C_{10}$ cycloalkyloxy group which may be substituted, a $C_7-C_{12}$ aralkyl group which may be substituted, or a $C_7-C_{12}$ aralkyloxy group which may be substituted.

7. Trans-4-amino-[(S)-N—[(S)-2-propoxycarbonylamino-3-isopropylthio-3-methyl-butanoyl]prolyl]aminomethylcyclohexane or a salt thereof, or a hydrate thereof. or a solvate thereof.

8. Trans-4- amino-[(S)-N-[(S)-2-ethoxycarbonylamino-3-isopropylthio-3-methyl-butanoyl]prolyl]aminomethylcyclohexane or a salt thereof, or a hydrate thereof or a solvate thereof.

9. A pharmaceutical composition comprising a substance selected from the group consisting of the compound and the salt thereof, and the hydrate thereof and the solvate thereof according to claim 1 together with a pharmaceutically acceptable additive.

10. A method for manufacturing a pharmaceutical composition, comprising:

combining at least one of the compound, salt thereof, hydrate thereof, and solvate thereof of claim 1, with a pharmaceutically acceptable additive.

11. A method for inhibiting proteases, comprising:

administering a therapeutically effective amount of at least one of the compound, salt thereof, hydrate thereof, and solvate thereof of claim 1.

12. A method of inhibiting coagulation, comprising:

administering a therapeutically effective amount of the pharmaceutical composition of claim 9.

* * * * *

UNITED STATES PATENT AND TRADEMARK OFFICE
CERTIFICATE OF CORRECTION

PATENT NO. : 6,239,150 B1
DATED : May 29, 2001
INVENTOR(S) : M. Oshima et al.

It is certified that error appears in the above-identified patent and that said Letters Patent is hereby corrected as shown below:

Column 38,
Lines 25-26, delete "or a salt thereof, or a hydrate thereof" (second occurrence).
Line 55, "where" should be -- wherein --.

Column 39,
Line 10, "$C_1C_6$" should be -- $C_1$-$C_6$ --.

Column 40,
Line 10, after "thereof" (first occurrence) delete " . ".

Signed and Sealed this

Thirteenth Day of August, 2002

Attest:

JAMES E. ROGAN
Attesting Officer
Director of the United States Patent and Trademark Office